United States Patent
Morton et al.

(10) Patent No.: US 7,326,793 B2
(45) Date of Patent: Feb. 5, 2008

(54) PROCESS FOR THE PREPARATION OF DIKETOPYRROLOPYRROLES

(75) Inventors: Colin Morton, Basel (CH); David Macdonald Smith, Fife (GB); Vincent Ruffieux, Marly (CH)

(73) Assignee: Ciba Specialty Chemicals Corporation, Tarrytown, NY (US)

( * ) Notice: Subject to any disclaimer, the term of this patent is extended or adjusted under 35 U.S.C. 154(b) by 556 days.

(21) Appl. No.: 10/485,840

(22) PCT Filed: Sep. 3, 2002

(86) PCT No.: PCT/EP02/09792

§ 371 (c)(1),
(2), (4) Date: Feb. 4, 2004

(87) PCT Pub. No.: WO03/022848

PCT Pub. Date: Mar. 20, 2003

(65) Prior Publication Data

US 2004/0171847 A1    Sep. 2, 2004

(30) Foreign Application Priority Data

Sep. 11, 2001 (EP) .................. 01810875
Dec. 20, 2001 (EP) .................. 01811249
Mar. 22, 2002 (EP) .................. 02405223

(51) Int. Cl.
*C07D 403/04* (2006.01)
*C07D 401/04* (2006.01)
*C07D 487/04* (2006.01)

(52) U.S. Cl. ............ 548/453; 544/295; 544/296; 546/276.7

(58) Field of Classification Search .......... 548/453; 546/276.7; 544/295, 296
See application file for complete search history.

(56) References Cited

U.S. PATENT DOCUMENTS

| 4,585,878 | A |   | 4/1986  | Jost et al. ............ 548/453 |
| 5,354,869 | A | * | 10/1994 | Langhals et al. ........ 548/453 |
| 5,424,157 | A |   | 6/1995  | Miyamoto et al. ........ 430/73 |
| 5,847,156 | A |   | 12/1998 | Eldin et al. ........... 548/453 |

FOREIGN PATENT DOCUMENTS

EP    1087005    3/2001

OTHER PUBLICATIONS

H. Langhals et al., Liebigs Ann.: Organic and Bioorganic Chemistry, vol. 5, No. 5, (1996), pp. 679-682.

* cited by examiner

*Primary Examiner*—James O. Wilson
*Assistant Examiner*—Ebenezer Sackey
(74) *Attorney, Agent, or Firm*—Shiela A. Loggins

(57) ABSTRACT

The present invention relates to a process for the preparation of diketopyrrolopyrroles of the formula (I), wherein A1, A2, A3 and A4 are as defined in the description of the present invention, to new diketopyrrolopyrroles of the general formula I obtainable by the process, and the use of the new diketopyrrolopyrroles of the general formula I for the preparation of inks, colorants, pigmented plastics for coatings, non-impact-printing material, color filters, cosmetics, polymeric ink particles, toners, dye lasers and electroluminescent devices, or as fluorescent markers for immunoassays and fluorescent tracers for leak detection of fluids. Furthermore the present invention relates to diketopyrrolopyrrole analogues of the general formula (II), wherein A1, A2 and A3 are defined in the description of the present invention, which are intermediates in the process for the preparation of diketopyrrolopyrroles of the formula I and can be used as crystal growth regulators

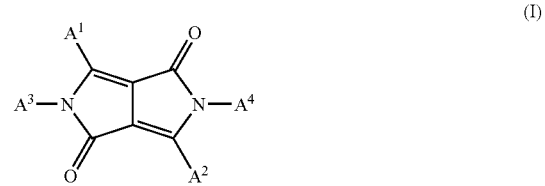

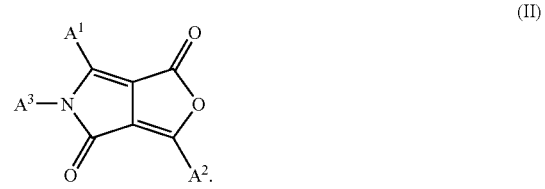

2 Claims, No Drawings

PROCESS FOR THE PREPARATION OF DIKETOPYRROLOPYRROLES

The present invention relates to a process for the preparation of diketopyrrolopyrroles ("DPPs") of the formula I, to new diketopyrrolopyrroles of the general formula I obtainable by the process, and the use of the new diketopyrrolopyrroles of the general formula I for the preparation of inks, colorants, pigmented plastics for coatings, non-impact-printing material, color filters, cosmetics, polymeric ink particles, toners, dye lasers and electroluminescent devices, or as fluorescent markers for immunoassays and fluorescent tracers for leak detection of fluids.

Furthermore the present invention relates to diketopyrrolopyrrole analogues of the general formula II, which are intermediates in the process for the preparation of diketopyrrolopyrroles of the formula I and can be used as crystal growth regulators.

DPP Compounds of the formula

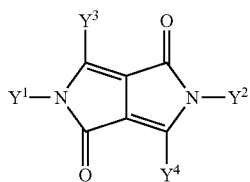

(X)

are known:

Compounds of the formula X in which $Y^1$ and $Y^2$ denote hydrogen and $Y^3$ and $Y^4$ denote identical or different isocyclic or heterocyclic aromatic radicals are known as red pigments from EP-B-61,426.

U.S. Pat. No. 5,973,146 relates to aminated diketobis(aryl or heteroaryl)pyrrolo-pyrroles and their use as photoconductive substances.

EP-A-1 087005 relates to fluorescent diketopyrrolopyrroles of the formula I'

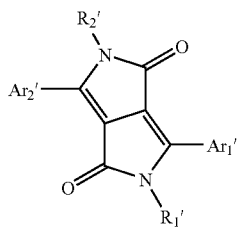

I' wherein $R_1'$ and $R_2'$, independently from each other, stand for $C_1$-$C_{25}$-alkyl, allyl which can be substituted one to three times with $C_1$-$C_3$alkyl or $Ar_3'$, —$CR_3'R_4'$—$(CH_2)_{m'}$—$Ar_3'$, wherein $R_3'$ and $R_4'$ independently from each other stand for hydrogen or $C_1$-$C_4$alkyl, or phenyl which can be substituted one to three times with $C_1$-$C_3$ alkyl, $Ar_3'$ stands for phenyl or 1- or 2-naphthyl which can be substituted one to three times with $C_1$-$C_8$alkyl, $C_1$-$C_8$alkoxy, halogen or phenyl, which can be substituted with $C_1$-$C_8$alkyl or $C_1$-$C_8$alkoxy one to three times, and m' stands for 0, 1, 2, 3 or 4, and wherein $C_1$-$C_{25}$alkyl or —$CR_3'R_4'$—$(CH_2)_{m'}$—$Ar_3$, can be substituted with a functional group capable of increasing the solubility in water such as a tertiary amino group, —$SO_3^-$, or $PO_4^{2-}$, $Ar_1'$ and $Ar_2'$, independently from each other, stand for an aryl or heteroaryl group. The DPP compounds can be used for the preparation of inks, colorants, pigmented plastics for coatings, non-impact-printing material, color filters, cosmetics, or for the preparation of polymeric ink particles, toners, dye lasers and electroluminescent devices. EP-A-1087006 describes electroluminescent devices comprising the DPP compounds of formula (I'). The DPPs exemplified in EP-A-1087005 and EP-A-1087006 are symmetrically substituted at the nitrogen atoms of the DPP basic unit.

EP-A-499 011 discloses organic electroluminescent elements, comprising a compound of formula X wherein $Y^3$ and $Y^4$ are independently of each other a 3-pyridyl or 4-pyridyl residue or a substituted or unsubstituted phenyl group and $Y^1$ and $Y^2$ are independently of each other hydrogen, $C_1$-$C_{18}$alkyl, $C_3$-$C_{18}$-alkenyl or a phenylalkyl group having 1 to 5 carbon atoms in the alkyl. The exemplified DPPs, 2,5-dihydro-2,5-dimethyl-3,6-diphenylpyrrolo[3,4-c]pyrrole-1,4-dione and 2,5-dihydro-2,5-dimethyl-3,6-di(2'-methoxyphenyl)pyrrolo[3,4-c]pyrrole-1,4-dione (example 8 and 10, respectively), are symmetrically substituted at the nitrogen atoms of the DPP basic unit.

WO 98/33862 describes the use of a DPP-compound of formula

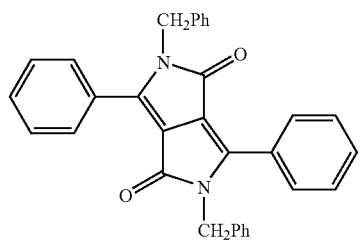

as a guest molecule in electroluminescent devices [example B2].

EP-A-811 625 discloses DPP compounds of the formula

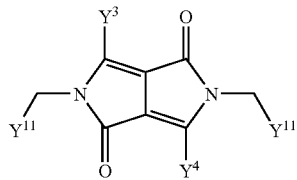

wherein $Y^{11}$ is a quinacridone or DPP radical.

WO96/08537 relates to a process for preparing N-methylated organic pigments.

EP-A-467 846 relates to electrochromic compositions containing at least one DPP derivative.

The DPP derivatives are symmetrically substituted at the nitrogen atoms of the DPP basic unit or one nitrogen atom is substituted by hydrogen and the other nitrogen is substituted by a group $(CH_2)_p$-L, wherein p is an integer of 1 to 6 and L is a sulfonic acid, a phosphonic acid, a carboxylic acid group or a salt thereof, or an ammonium group.

WO98/25927 relates to liquid crystalline diketopyrrolopyrroles, which are symmetrically substituted at the nitrogen atoms of the DPP basic unit.

The compounds of the above-mentioned general formula X can be prepared by various known processes:

According to the process described in EP-B-61,426, a nitrile of the formula $Y^3$—CN is reacted, if desired together with a nitrile of the formula $Y^4$—CN, with bromoacetic ester and zinc, a compound of the above-mentioned formula where $Y^1$=$Y^2$=H being formed. Better yields are obtained if 2 mol of the nitrile $Y^3$—CN or the nitrile mixture $Y^3$—CN/$Y^4$—CN are reacted in a manner known per se with 1 mol of a diethyl succinate in an organic solvent in the presence of a strong base at elevated temperature, cf. EP-B-94,911.

U.S. Pat. No. 4,585,878 relates to N-subsbtuted 1,4-diketopyrrolo[3,4-c]pyrroles of the above-mentioned general formula in which $Y^3$ and $Y^4$ are isocyclic aromatic or heterocyclic aromatic radicals, in particular unsubstituted or substituted phenyl or naphthyl, and $Y^1$ and $Y^2$ are independently of one another alkyl, alkoxycarbonyl, phenyl, benzoyl or benzyl, which are suitable for dyeing high molecular weight organic material.

The compounds of the above-mentioned formula are prepared
(a) by reacting the compound of the formula

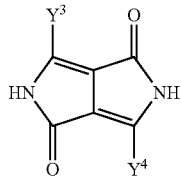

with a compound containing the radicals $Y^1$ and/or $Y^2$ as leaving groups, in an organic solvent, or
(b) by reacting 2 moles of a compound of the formula

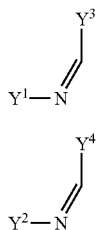

(XI)

(XII)

or one mole each of the compounds of the formulae (XI) and (XII), with 1 mole of a succinic acid diester in the presence of a base and an organic solvent (cf. J. Chem. Soc. 1976, page 5) and then dehydrogenating the product. The exemplified DPPs, for example 2,5-dihydro-2,5-dibenzyl-3,6-diphenylpyrrolo[3,4-c]pyrrole-1,4-dione and 2,5-dihydro-2,5-bis(4'-chlorophenyl-3,6-di(4'-chlorophenylpyrrolo[3,4c] pyrrole-1,4-dione (example 8 and 10, respectively), are symmetrically substituted at the nitrogen atoms of the DPP basic unit. U.S. Pat. No. 5,354,869 relates to 3,6-bis-(2'-methoxyphenyl)-2,5-dihydro-2,5-dimethyl-pyrrolo[3,4-C] pyrrole-1,4-dione and its use as storage media in optical memories. Described is also a process for the preparation of the compounds of the general formula X which consists in reacting furanofurandione of the general formula

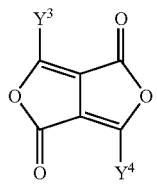

with a primary amine of the general formula $Y^1NH_2$ or with a mixture of primary amines $Y^1NH_2/Y^2NH_2$ wherein $Y^1$, $Y^2$, $Y^3$ and $Y^4$ denote hydrogen, aromatic radicals, heteroaromatic radicals, heterocyclic radicals or other non-water-solubilising radicals. The exemplified DPPs, for example 2,5-dihydro-2,5-diphenyl-3,6-diphenylpyrrolo[3,4-c]pyrrole-1,4-dione and 2,5-dihydro-2,5-bis(4'-methylphenyl-3,6-diphenylpyrrolo[3,4-c]pyrrole-1,4-dione (example 13 and 14, respectively), are symmetrically substituted at the nitrogen atoms of the DPP basic unit. In Liebigs Ann. 1996, 679-682H. Langhals et al. disclose the synthesis of N-arylpyrrolopyrrolediones.

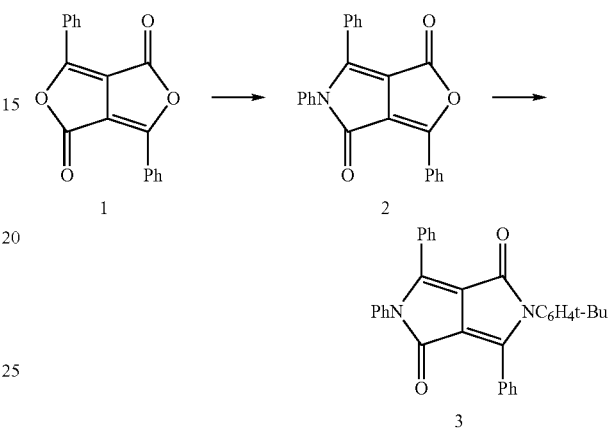

Condensation of 1 with aniline yields the intermediate 2 [yield: 15.6%] as an orange powder with a weak yellow solid state fluorescence. The intermediate 2 was condensed with para-t-butylaniline yielding the unsymmetric substituted dye 3 [yield: 2.5%]. The overall yield of the disclosed synthesis is very low.

In view of the above-mentioned state of the art it is the object of the present invention to provide a new process for the preparation of diketopyrrolopyrroles which in particular make it possible to obtain DPPs which are unsymmetrically substituted at the nitrogen atoms of the DPP basic unit in an acceptable yield.

This object has surprisingly been solved by a process for the preparation of diketopyrrolopyrroles of the general formula

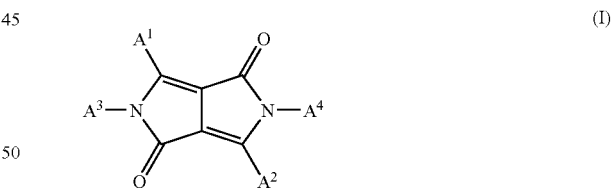

(I)

comprising reacting a compound of the formula

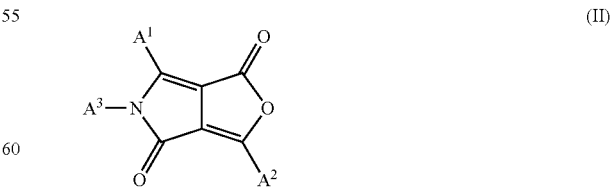

(II)

with a primary amine of the formula $A^4\text{-}NH_2$ (III),
wherein $A^1$ and $A^2$ are $C_1$-$C_{18}$alkyl, $C_2$-$C_{18}$alkenyl, $C_2$-$C_{18}$alkynyl, $C_5$-C-cycloalkyl, $C_5$-$C_8$cycloalkenyl, aryl or heteroaryl, A³ is hydrogen, C₁-C₁₈alkyl, cyanomethyl, Ar³, —CR³⁰R³¹—(CH₂)ₘ—Ar³ or Y-R₃₂, wherein R₃₀ and R³¹ independently of each other stand for hydrogen or C₁-C₄alkyl, or phenyl which can be substituted up to three times with C₁-C₃alkyl, Ar³ stands for aryl, C₅-C₈cycloalkyl, C₅-C₈cycloalkenyl or heteroaryl, which can be substituted one to three times with C₁-C₈alkyl, C₁-C₈alkoxy, halogen or phenyl, which can be substituted with C₁-C₈alkyl or C₁-C₈alkoxy one to three times, and m stands for 0, 1, 2, 3 or 4, Y is —C(O)—, —C(O)O—, —C(O)NH— or —SO₂—, —SO₂NH— and R³² is C₁-C₁₈alkyl, C₁-C₁₈alkoxy, —NH—C₁-C₁₈alkyl, Ar³, or aralkyl, and A⁴ is C₁-C₁₆alkyl or Ar³.

The reaction between the compound of the general formula II and the primary amine or the mixture of primary amines is carried out in a suitable inert solvent or dispersant. Suitable solvents or dispersants are, for example, ethers, in particular those having 2 to 8 carbon atoms in the molecule, such as, for example, diethyl ether, methyl ethyl ether, di-n-propyl ether, diisopropyl ether, methyl n-butyl ether, methyl tert-butyl ether, ethyl n-propyl ether, di-n-butyl ether, tetrahydrofuran, 1,4-dioxane, 1,2-dimethoxyethane, bis-B-methoxyethyl ether; oligoethylene glycol dimethyl ethers, such as, for example, pentaglyme; aliphatic hydrocarbons, such as, for example, hexane, heptane, low- and high-boiling petroleum ethers; cycloaliphatic hydrocarbons, such as, for example, cyclohexane, methylcyclohexane, tetralin, decalin; aromatic hydrocarbons, such as, for example, benzene, toluene, o-, m- and p-xylene, ethylbenzene; halogenated aliphatic or aromatic hydrocarbons, such as, for example, methylene chloride, chloroform, carbon tetrachloride, chlorobenzene, dichlorobenzene; nitriles, such as, for example, acetonitrile; amides, such as, for example, dimethylformamide, dimethylacetamide, N-methylpyrrolidone; hexamethylphosphoric triamide; and sulfoxides, such as, for example, dimethyl sulfoxide. Mixtures of various solvents can also be used.

The reaction is preferably carried out in a dipolar or non-polar aprotic solvent. Examples of preferred aprotic solvents are: dimethylformamide, dimethyl sulfoxide, hexamethylphosphoric triamide, sulfolane, N-methylpyrrolidone, tetramethylurea, acetonitrile, ethylene glycol dimethyl ether, ethylene glycol diethyl ether, diethylene glycol dimethyl ether and triethylene glycol dimethyl ether, nitromethane, 1,3-dimethyl-3,4,5,6-tetrahydro-2(1H)-pyrimidinone (DMPU), 1,3-dimethyl-2-imidazolidinone, benzonitrile, nitrobenzene, chloroform, carbon tetrachloride and methylene chloride. Particularly preferred aprotic solvents are chloroform, carbon tetrachloride and methylene chloride, of which chloroform is particularly preferred. The reaction between the compound of the general formula II and the primary amine III is carried out in the presence of a dehydrating agent. Examples of suitable dehydrating or water-eliminating agents of this type are: N,N'-disubstituted carbodiimides, in particular if they contain at least one secondary or tertiary alkyl radical, such as, for example, diisopropyl-, dicyclohexyl- or N-methyl-N'-tert.-butylcarbodiimide (cf. "The Chemistry of Ketenes, Allenes and Related Compounds", Part 2, Editor: S. Patai, John Wiley & Sons 1980, 722-753). Dicyclohexylcarbodiimide is particularly suitable.

The reaction between the compound of the formula II and the primary amine III can be carried out, for example, at temperatures from −10° C. up to the boiling point of the solvent or solvent mixture used. In many cases it is carried out at −10 to 30° C. and preferably at room temperature. 0.9 to 1.4 mol, preferably 1.0 to 1.3 mol of the primary amine III are in general employed per mole of compound of the general formula II. The reaction can be catalyzed by adding a strong non-aqueous acid such as trifluoroacetic acid.

The primary amines III are known or can be easily prepared by the methods known for the preparation of these class of compound.

The starting compound of the formula II, wherein A³ is different from a hydrogen atom, is obtained by reacting a compound of the formula

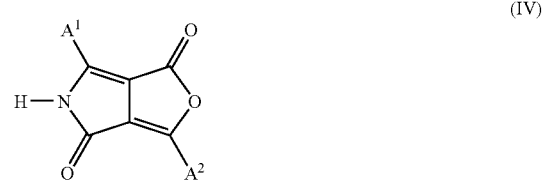

(IV)

with a compound of the formula A³-X (V), wherein A¹, A² and A³ have the meanings as given above and X is a leaving group. The reaction between the compound of the general formula IV and the compound of the formula V is carried out in a suitable inert solvent or dispersant such as tetrahydrofuran or diethyl ether, in the presence of a base such as sodium hydride at a temperature ranging from 20° C. to the boiling point of the solvent. The term "eaving group" means a group, such as iodine, bromine or chlorine, benzene- or p-toluenesulfonate. Processes for the introduction of A³ into compounds of the formula IV are described, for example, in U.S. Pat. No. 4,585,878.

Suitable alkylating agents are, for example, alkyl halides, in particular alkyl iodides, alkyl esters, in particular alkyl esters of sulfonic acids, such as, for example, alkyl esters of benzene- or p-toluenesulfonic acid. Suitable arylating agents are for example iodoaryl compounds such as iodobenzene.

The starting compound of the formula IV is obtained by heating a compound of the formula

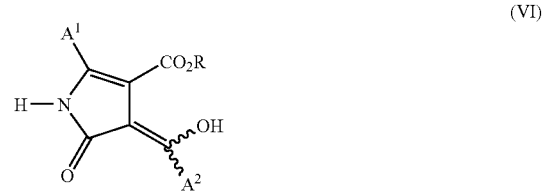

(VI)

in an inert solvent, wherein A¹ and A² have the meanings as given above and R is C₁-C₁₈alkyl, in particular C₁-C₄alkyl, aryl, in particular phenyl, or aralkyl, in particular benzyl, which can be substituted one to three times with C₁-C₈alkyl, C₁-C₈alkoxy, or halogen. Examples of inert solvents include, but are not limited to aromatic solvents, like biphenyl, para-, meta or ortho-terphenyl, dibenzyltoluene, α-methyl- or β-methyl-naphthalene, cyclic carbonates, like 1,3-dioxolan-2-one, ketones, like acetophenone or benzophenone, γ-butyrolactone and ethylene glycols, like Phe-Cellosolve or Bu-Cellosove, or mixtures thereof, in particular mixtures of di- and triarylethers (Dowtherm A®). In a preferred embodiment the compound of the formula VI is dissolved in Dowtherm A® and heated for about 0.5 to 240 hours at a temperature of 220 to 260° C., preferably 230-240° C.

The present invention is also directed to the compounds of the formula VI which are novel intermediates in the synthesis of the diketopyrrolopyrroles of the formula I and the diketopyrrolopyrrole analogues of the formula II, respectively.

The starting compound of the formula VI is obtained by reacting a compound of the formula

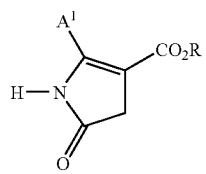

(VII)

with an ester of the formula $A^2\text{-}CO_2R$ (VIII) in the presence of a base, such as for example sodium tert.-amylate/tert.-amylalcohol at a temperature ranging from 25° C. to the boiling point of the solvent, wherein R, $A^1$ and $A^2$ have the meanings as given above.

The starting compounds of the formula VII are known or can be prepared in analogy to processes described in U.S. Pat. No. 4,681,971, U.S. Pat. No. 4,749,795, U.S. Pat. No. 4,720,305 and U.S. Pat. No. 4,659,775.

Alternatively, compounds of the formula

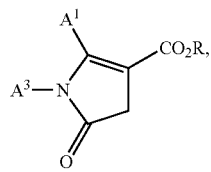

(VII)

wherein $A^3$ is different from a hydrogen atom and is in particular aryl, can be prepared by a copper catalyzed decomposition of diazoacetates in the presence of enaminoamides (G. Maas, A. Müller, J. prakt. Chem. 340 (1998) 315-322):

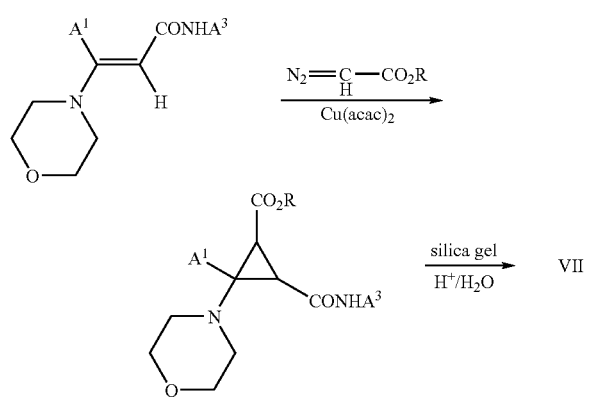

The compounds of the formula VII, wherein $A^3$ is different from a hydrogen atom and is in particular aryl, can be reacted to compounds of the formula I as described above.

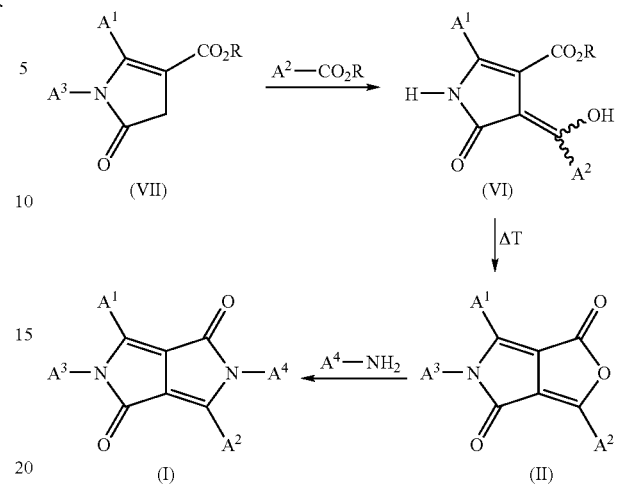

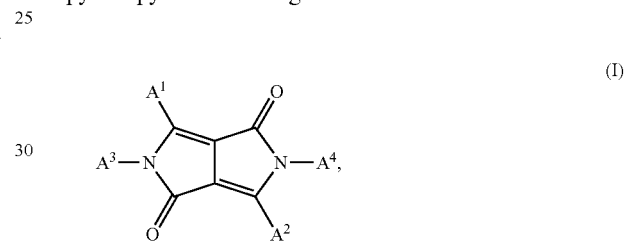

Furthermore, the present invention relates to novel diketopyrrolopyrroles of the general Formula (I)

wherein $A^1$, $A^2$ and $A^3$ have the meanings as given above and $A^4$ is $Ar^3$, wherein preferably $A^4$ is different from $A^3$.

The DPPs of the general formula I show a high heat stability, a good solubility in polymers, hydrocarbon based fuels, lubricants, and water, a high light stability, and the ability to be used in plastics, especially polyamides, without decomposition and loss of lightfastness, and in paints; and can show photo- and electroluminescence as well as solid state fluorescence. The residues $A^1$ and $A^2$ are in general selected from $C_1\text{-}C_{18}$alkyl, $C_2\text{-}C_{18}$alkenyl, $C_2\text{-}C_{18}$alkynyl, $C_5\text{-}C_8$cycloalkyl, such as cyclopentyl, cyclohexyl, cycloheptyl and cyclooctyl, in particular cyclohexyl, $C_5\text{-}C_8$cycloalkenyl, such as cyclopentenyl, cyclopentadienyl and cyclohexenyl, in particular cyclohex-3-enyl, aryl and heteroaryl.

Diketopyrrolopyrroles, wherein $A^1$ and $A^2$ are radicals of the formula

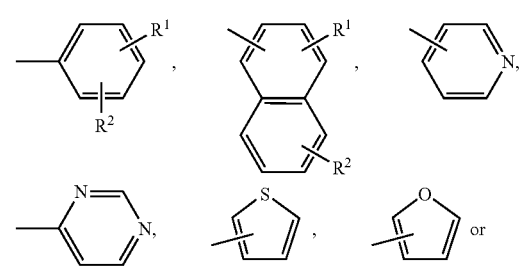

-continued

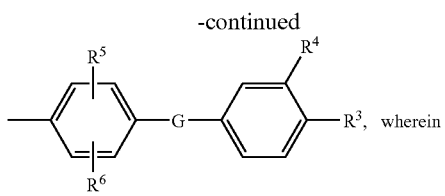

R¹ and R² are independently of each other hydrogen, halogen, $C_1$-$C_{18}$alkyl, $C_1$-$C_{18}$alkoxy, $C_1$-$C_{18}$alkylmercapto, di($C_1$-$C_{18}$alkyl)amino, $C_1$-$C_{18}$alkylamino, $C_1$-$C_8$alkoxycarbonyl, $C_1$-$C_{18}$alkylaminocarbonyl, —CN, —$NO_2$, trifluoromethyl, $C_5$-$C_8$cycloalkyl, —C=N—($C_1$-$C_{18}$alkyl), phenyl,

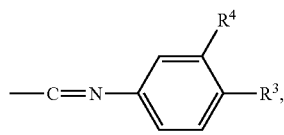

imidazolyl, pyrrazolyl, triazolyl, piperazinyl, pyrrolyl, oxazolyl, benzoxazolyl, benzothiazolyl, benzimidazolyl, morpholinyl, piperidinyl or pyrrolidinyl, 13 $CONX^5X^6$, —C(O)OX⁷ or —$SO_2X^9$; wherein $X^5$ and $X^6$ are hydrogen, linear or branched $C_{1-10}$-alkyl, $C_{5-10}$-cycloalkyl or $C_{6-10}$-aryl, $X^7$ is hydrogen, linear or branched $C_{1-10}$-alkyl, $C_{5-10}$-cycloalkyl or $C_{6-10}$-aryl, $X^9$ is hydrogen, linear or branched $C_{1-10}$-alkyl, $C_{5-10}$-cycloalkyl, $C_{7-10}$-aralkyl, $C_{6-10}$-aryl or —$NX^{10}X^{11}$, wherein $X^{10}$ and $X^{11}$ are hydrogen, linear or branched $C_{1-10}$-alkyl, $C_{7-10}$-aralkyl or $C_{6-10}$-aryl, G is —$CH_2$—, —CH($CH_3$)—, —C($CH_3$)$_2$—, —CH=N—, —N=N—, —O—, —S—, —$SO_2$—, —CONH— or —NR⁷—, R³ and R⁴ are independently of each other hydrogen, halogen, $C_1$-$C_6$alkyl, $C_1$-$C_{18}$alkoxy or —CN, R⁵ and R⁶ are independently of each other hydrogen, halogen or $C_1$-$C_6$alkyl, and R⁷ is hydrogen or $C_1$-$C_6$alkyl are preferred, wherein radicals of the formula

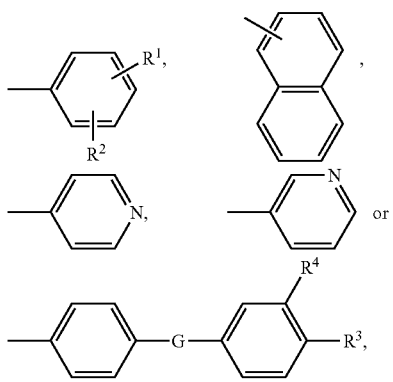

wherein R¹ and R² are independently of each other hydrogen, chloro, bromo, $C_1$-$C_4$alkyl, $C_1$-$C_6$alkoxy, $C_1$-$C_6$alkylamino, phenyl or CN,
G is —O—, —NR⁷—, —N=N— or —$SO_2$—,
R³ and R⁴ are hydrogen, and
R⁷ is hydrogen, methyl or ethyl are further preferred and diketopyrrolopyrrole analogues, wherein A¹ and A² are radicals of the formula

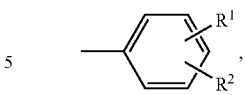

wherein R¹ and R² are independently of each other hydrogen, methyl, tert-butyl, chloro, bromo, phenyl or CN are particularly preferred for the preparation of inks, colorants, pigmented plastics for coatings, non-impact-printing material, color filters, cosmetics, polymeric ink particles, toners.

In the case of electroluminescence applications the following residues are preferred for A¹ and A²:

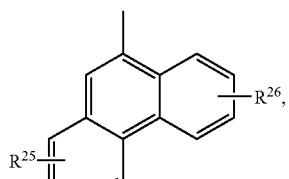

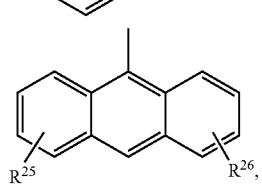

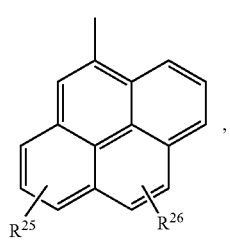
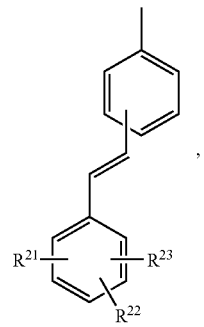

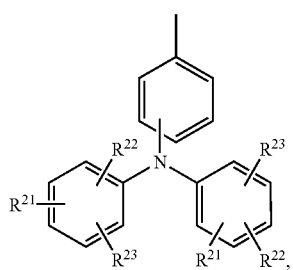

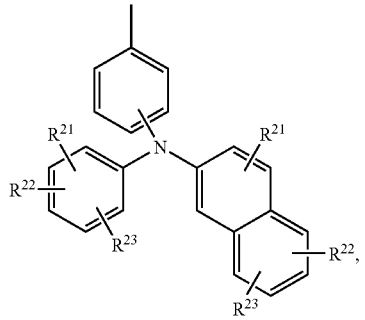

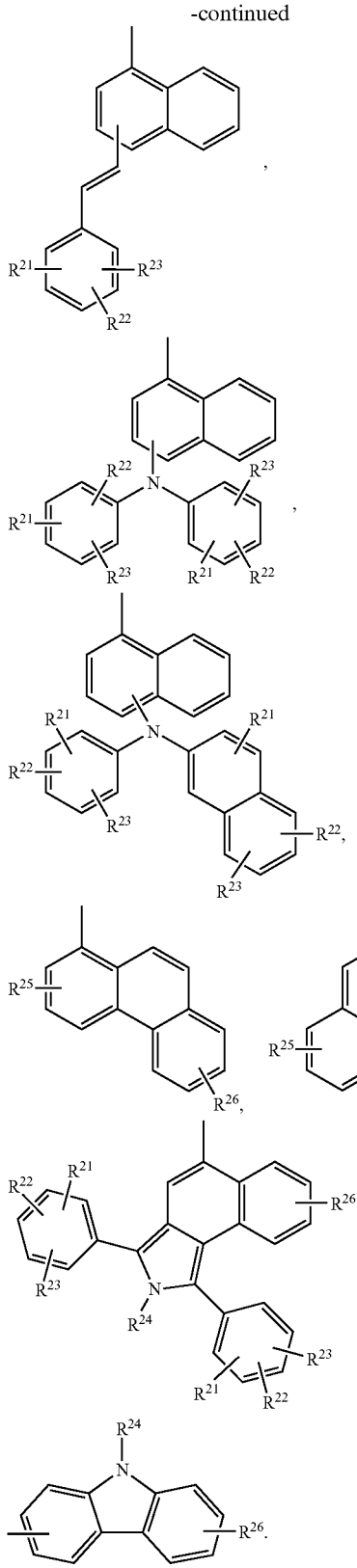

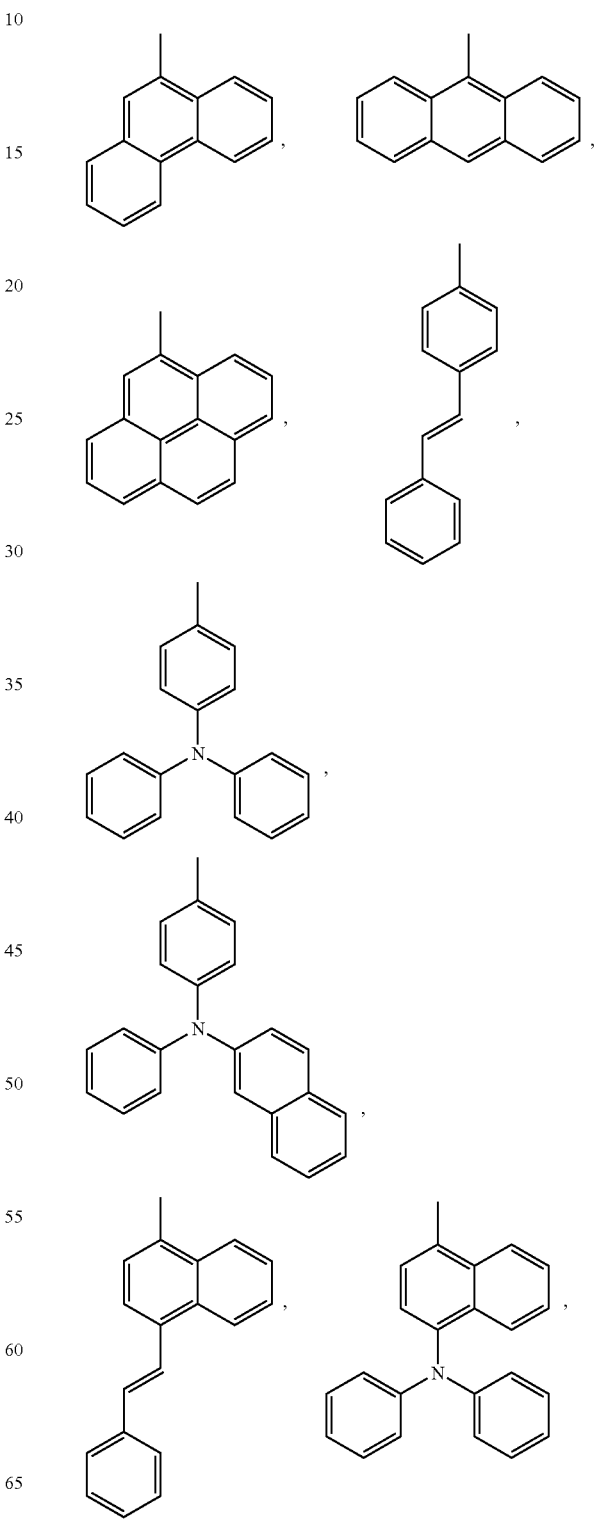

wherein $R^{21}$, $R^{22}$, $R^{23}$, $R^{25}$ and $R^{26}$ are independently of each other hydrogen, $C_1$-$C_8$alkyl, a hydroxyl group, a mercapto group, $C_1$-$C_8$alkoxy, $C_1$-$C_8$alkylthio, halogen, halo-$C_1$-$C_8$alkyl, a cyano group, an aldehyde group, a ketone group, a carboxyl group, an ester group, a carbamoyl group, an amino group, a nitro group, a silyl group or a siloxanyl group and $R^{24}$ is a $C_1$-$C_6$alkyl group. Preferably $R^{21}$, $R^{22}$, $R^{23}$, $R^{25}$ and $R^{26}$ are independently of each other hydrogen, $C_1$-$C_8$alkyl, $C_1$-$C_8$alkoxy or $C_1$-$C_8$alkylthio, wherein the following residues are particularly preferred:

-continued

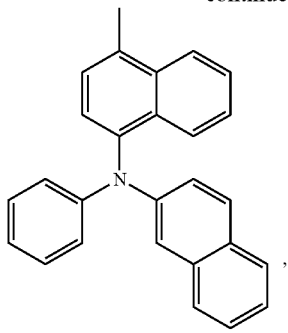

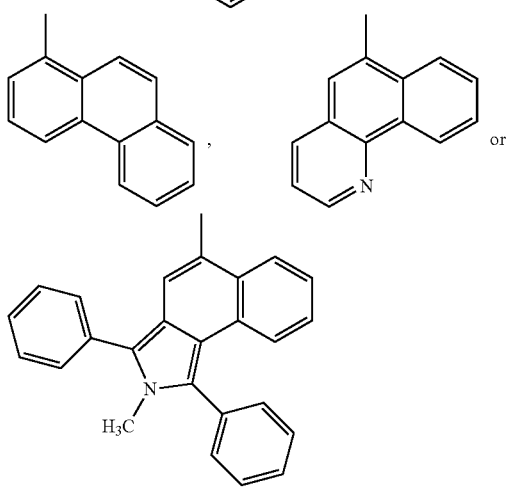

The residue A³ is in general selected from hydrogen, C₁-C₁₈alkyl, cyanomethyl, Ar³, —CR³⁰R³¹—(CH₂)ₘ—Ar³ or Y—R³², wherein R³⁰ and R³¹ independently of each other stand for hydrogen or C₁-C₄alkyl, or phenyl which can be substituted up to three times with C₁-C₃alkyl, Ar³ stands for aryl, in particular phenyl or 1- or 2-naphthyl, C⁵-C₈cycloalkyl, such as cyclopentyl, cyclohexyl, cyclohoptyl and cyclooctyl, in particular cyclohexyl, C₅-C₈cycloalkenyl, in particular cyclopentenyl, cyclopentadienyl and cyclohexenyl, or heteroaryl, which can be substituted one to three times with C₁-C₈alkyl, C₁-C₈alkoxy, halogen or phenyl, which can be substituted with C₁-C₈alkyl or C₁-C₈alkoxy one to three times, and m stands for 0, 1, 2, 3 or 4, Y is —C(O)—, —C(O)O—, —C(O)NH—, —SO₂NH— or —SO₂— and R³² is C₁-C₁₈alkyl, Ar³, or aralkyl.

A³ is preferably hydrogen, C₁-C₈alkyl such as methyl, ethyl, n-propyl, isopropyl, n-butyl, sec.-butyl, isobutyl, tert.-butyl, n-pentyl, 2-pentyl, 3-pentyl, 2,2-dimethylpropyl, n-hexyl, n-heptyl, n-octyl, 1,1,3,3-tetiamethylbutyl and 2-ethylhexyl, Y—R³² wherein Y is —C(O)— and R³² is

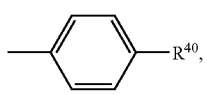

wherein R⁴⁰ is C₁-C₄alkyl, —O—C₁-C₄alkyl, or —S—C₁-C₄alkyl and —(CH₂)ₘ—Ar wherein m is 1 and Ar is a group of the formula

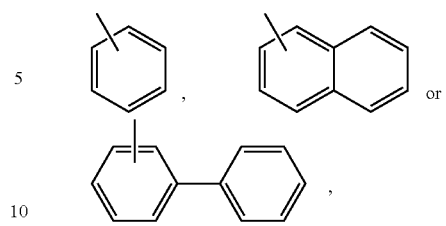

which can be substituted one to three times with C₁-C₈alkyl, C₁-C₈alkoxy, halogen or phenyl.

Examples of preferred residues Ar are

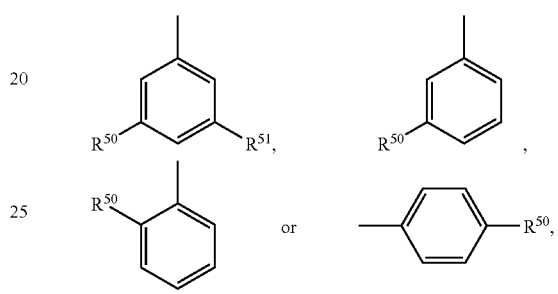

wherein R⁵⁰ and R⁵¹ are independently of each other methyl, ethyl, n-propyl, isopropyl, n-butyl, sec.-butyl, isobutyl, tert.-butyl, methoxy, ethoxy, isopropoxy, tert.-butoxy or chlorine.

The residue A⁴ is in general selected from C₁-C₁₈alkyl or Ar³, in particular Ar³, wherein A⁴ is preferably

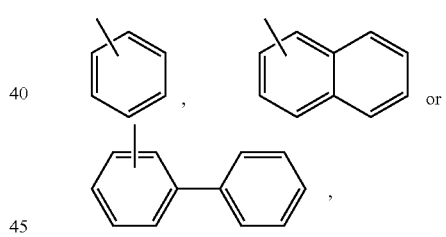

which can be substituted one to three times with C₁-C₈alkyl, C₁-C₈alkoxy, halogen or phenyl.

Moreover, the present invention relates to diketopyrrolopyrrole analogues of the formula (II)

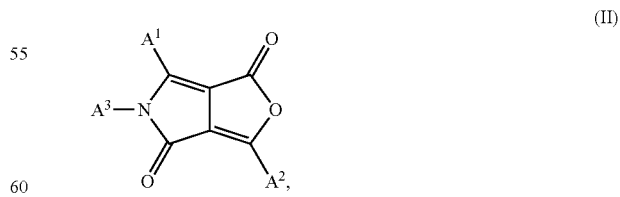

wherein A¹, A² and A³ have the meanings as given above, with the proviso that 3,5,6-triphenyl-1H-furo[3,4c]pyrrol-1, 4-(5H)-dion is excluded.

The diketopyrrolopyrrole analogues of the formula II are intermediates in the process for the preparation of the diketopyrrolopyrroles of the formula I and can be used as crystal growth regulators, wherein the term "regulating the crystal growth" refers to controlling the synthesis of pigment particles to have a suitable pigmentary size and/or a narrow particle size distribution as well as directing the growth of the crystals to generate particles of a specifically desired shape, such as platelet, needle, cubic, leaflet, prismatic and other geometric forms and/or of a specifically desired rheology. Consequently, the better control of the crystal growth allows gaining samples with a narrower particle size distribution and/or a better crystal shape, or both together. The effect can be influenced by the chemical structure of the organic pigment, the selection of the reaction media and the concentration and chemical structure of the inventive particle growth regulator.

Hence, a further aspect of the instant invention is directed to pigment compositions comprising a primary pigment and from about 0.1-20% of the diketopyrrolopyrrole analogue of the formula II (including 3,5,6-triphenyl-1H-furo[3,4-c]pyrrole-1,4-(5H)-dione), based on primary pigment weight. Preferred concentrations range from 1.0 to 10.0%, by weight of primary pigment. Although DPPs are preferred as primary pigment, the use of diverse pigment moieties is likewise available where the respective pigments are color compatible. Examples of applicable organic primary pigments are: anthraquinone, phthalocyanine, perinone, perylene, dioxazine, diketopyrrolopyrrole, thioindigo, isoindoline, isoindolinone, quinacridone, quinacridonequinone, flavanthrone, indanthrone, anthrapyrimidine or quinophthalone pigments, and solid solutions comprising these pigments. Pigments having good heat resistance and high transparency are especially suitable. Preferred organic pigments are quinacridones, phthalocyanines, anthraquinones, perylenes, diketopyrrolopyrroles, isoindolinones and indanthrones.

When the pigment compositions are prepared, the diketopyrrolopyrrole analogues of the formula II can be added during the pigment synthesis, during the fine dispersion process, before or after a finishing process by methods well-known in the art.

The diketopyrrolopyrrole analogues of formula II are in particular used as crystal growth regulator in a process for the direct preparation of DPP compounds of the formula

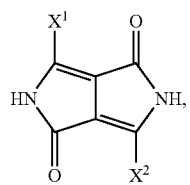

(X)

wherein $X^1$ and $X^2$ independently of each other are an unsubstituted or substituted isocyclic or heterocyclic aromatic radical. Said process comprises (a) heating an appropriate molar ratio of a disuccinate with a nitrile of the formula (II)

$X^1$—CN (XI)

or of the formula (III)

$X^2$—CN (XII)

or with mixtures of said nitriles, in an organic solvent and in the presence of a strong base, to form a product, (b) conditioning of the intermediate condensation product obtained in step (a) in water or a mixture of water and a water-miscible solvent, optionally in the presence of an inorganic acid to form the compound of formula (X), and (c) optionally conditioning of the product obtained in step (b) in an aprotic solvent, wherein a diketopyrrolopyrrole analogue of formula II is added in the heating step (a), the conditioning step (b) or (c).

Due to the presence of crystal growth regulors DPP particles exhibiting a higher opacity/hiding power than commercial pigments synthesized without growth controllers are obtained.

Hence, the present invention relates also to pigment compositions comprising a) a 1,4-diketopyrrolo[3,4-c]pyrrole of the formula X; and b) an effective crystal growth directing amount of a compound of formula II.

The particle growth regulator is present in an amount of between 0.1 and 10 weight %, based on the weight of the diketopyrrolopyrrole. A more useful range of particle growth regulator is from 0.5% to 4%, In particular 0.5% to 2% by weight of the particle growth regulator.

The expressions "direct" or "directly", when used herein to describe a preparatory process for a pigmentary product, means that the specific surface area of the pigmentary product will be within the range which makes it suitable for use as a pigment with specific desired properties. In order for the 1,4-diketopyrrolo[3,4-c]pyrroles of formula (I) to be suitable for direct use as a pigment, the surface area of the reaction product should be at least 15 meters$^2$/gram, for example in the range of from about 15 to about 50 m$^2$/gram, preferably from about 20 to 50 m$^2$/gram. The surface area can be measured by nitrogen absorption or another suitable method.

The radicals $X^1$ and $X^2$ may be the same or different, but are preferably identical. $X^1$ and $X^2$ as isocyclic aromatic radicals are preferably monocyclic to tetracyclic radicals, most preferably monocyclic or bicyclic radicals such as phenyl, diphenyl, naphthyl and the like. Heterocyclic aromatic radicals $X^1$ and $X^2$ are preferably monocyclic to tricyclic radicals. These radicals may be entirely heterocyclic or may contain a heterocyclic ring and one or more fused benzene rings, and the cyano group can be linked both to the heterocyclic and to the isocyclic moiety respectively. Examples of heterocyclic aromatic radicals are pyridyl, pyrimidyl, pyrazinyl, triazinyl, furyl, pyrrolyl, thiophenyl, quinolyl, cumarinyl, benzfuranyl, benzimidazolyl, benzoxazolyl, dibenzfuranyl, benzothiophenyl, dibenzothiophenyl, indolyl, carbazolyl, pyrazolyl, imidazolyl, oxazolyl, isoxazolyl, thiazolyl, indazolyl, benzthiazolyl, pyridazinyl, cinnolyl, quinazolyl, quinoxalyl, phthalazinyl, phthalazindionyl, phthalamidyl, chromonyl, naphtholactamyl, quinolonyl, ortho-sulfobenzimidyl, maleinimidyl, naphtharidinyl, benzimidazolonyl, benzoxazolonyl, benzthiazolonyl, benzthiazothionyl, quinazolonyl, quinoxalonyl, phthalazonyl, dioxopyrimidinyl, pyridonyl, isoquinolonyl, isoquinolinyl, isothiazolyl, benzisoxazolyl, benzisothiazolyl, indazolonyl, acridonyl, quinazolindionyl, quinoxalindionyl, benzoxazindionyl, benzoxazinonyl and naphthalimidyl. Both the isocyclic and the heterocyclic aromatic radicals may contain the customary non-watersolubilising substituents such as those described in U.S. Pat. No. 6,057,449.

Pyrrolo[3,4-c]pyrroles of the formula X, in which $X^1$ and $X^2$ independently of one another are a group of the formula

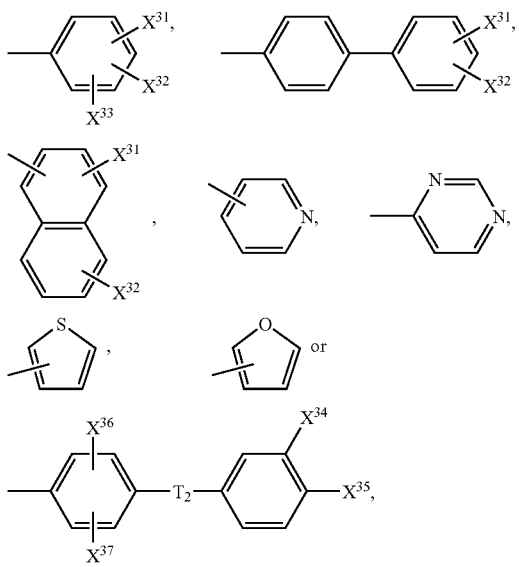

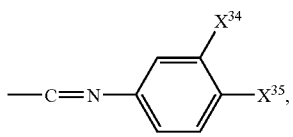

in which $X^{31}$, $X^{32}$ and $X^{33}$ independently of one another are hydrogen, halogen, $C_1$-$C_{24}$alkyl, $C_1$-$C_6$alkoxy, $C_1$-$C_{18}$alkylthio, $C_1$-$C_{18}$alkylamino, di($C_1$-$C_{18}$alkyl)amino, —CN, —NO$_2$, phenyl, trifluoromethyl, $C_5$-$C_6$cycloalkyl, —C=N—($C_1$-$C_{24}$alkyl), imidazolyl, pyrazolyl, triazolyl, piperazinyl, pyrrolyl, oxazolyl, benzoxazolyl, benzothiazolyl, benzimidazolyl, morpholinyl, piperidinyl or pyrrolidinyl, $T_2$ is —CH$_2$—, —CH(CH$_3$)—, —C(CH$_3$)$_2$—, —CH=N—, —N=N—, —O—, —S—, —SO—, —SO$_2$— or —NX$_{38}$—, $X^{34}$ and $X^{35}$ independently of one another are hydrogen, halogen, $C_{1-6}$-alkyl, $C_{1-6}$-alkoxy or —CN, $X^{36}$ and $X^{37}$ independently of one another are hydrogen, halogen or $C_{1-6}$-alkyl and $X^{38}$ is hydrogen or $C_1$-$C_6$-alkyl; are preferred and DPPs of the formula X, in which $X^1$ and $X^2$ are independently of each other a group of the formula

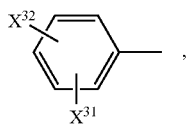

in which $X^{31}$ and $X^{32}$ independently of one another are hydrogen, methyl, tert-butyl, chlorine, bromine, CN or phenyl are especially preferred.

In particular, the starting materials employed are nitriles of the formula wherein each of $X^{20}$, $X^{21}$ and $X^{22}$, independently of one another, is hydrogen, fluorine, chlorine, bromine, carbamoyl, cyano, trifluoromethyl, $C_{2-10}$-alkylcarbamoyl, $C_{1-10}$-alkyl, $C_{1-10}$-alkoxy, $C_{1-10}$-alkylmercapto, $C_{2-10}$-alkoxycarbonyl, $C_{2-10}$-alkanoylamino, $C_{1-10}$-monoalkylamino, $C_{1-20}$-dialkylamino, phenyl or phenoxy, phenylmercapto, phenoxycarbonyl, phenylcarbamoyl or benzoylamino, each unsubstituted or substituted by halogen, $C_{1-4}$-alkyl or $C_{1-4}$alkoxy, with the proviso that at least one of $X^{20}$, $X^{21}$ or $X^{22}$ is hydrogen.

Preferably, the starting materials employed are nitriles of the formula XIa, wherein $X^{20}$ is hydrogen and both $X_{21}$ and $X^{22}$ are hydrogen, or one of $X^{21}$ or $X^{22}$ is chlorine, bromine, $C_{1-4}$-alkyl, cyano, $C_{1-4}$-alkoxy, or is phenyl, phenoxy, carbamoyl or $C_{1-4}$-alkylcarbamoyl, each unsubstituted or substituted by chlorine or methyl, or is phenylcarbamoyl which is unsubstituted or substituted by chlorine, methyl or methoxy, and the other is hydrogen. In a further preferred embodiment of the present process only one nitrile of formula (XI) or of formula (XII) is used.

A preferred embodiment of the present invention concerns a process wherein $X^1$ and $X^2$, each independently of the other, are phenyl or said phenyl substituted by one or two chlorine atoms, by one or two methyl groups, by methoxy, by trifluoromethyl, by cyano, by methpxycarbonyl, by methyl, by tert-butyl, by dimethylamino or by cyanophenyl; naphthyl, biphenylyl; pyridyl or said pyridyl substituted by amyloxy; furyl or thienyl, such as phenyl, 3-chlorophenyl, 4-chlorophenyl, 3,5-dichlorophenyl, 4-methylphenyl, 4-methoxyphenyl, 3-trifluoromethylphenyl, 4-trifluoromethylphenyl, 3-cyanophenyl, 4-cyanophenyl, 4-methoxycarbonylphenyl, 4-methylphenyl, 4-tert-butylphenyl, 4-dimethylaminophenyl, 4-(para-cyanophenyl)phenyl, 1-naphthyl, 2-naphthyl, 4-biphenylyl, 2-pyridyl, 6-amyloxy-3-pyridyl, 2-furyl or 2-thienyl.

The disuccinates include dialkyl, diaryl or monoalkyl-monoaryl succinates. The dialkyl and diaryl succinates may also be asymmetrical. However, it is preferred to use symmetrical disuccinates, most preferably symmetrical dialkyl succinates, most preferably symmetrical dialkyl succinates. If a diaryl or monoaryl-monoalkyl succinate is employed, aryl denotes preferably phenyl which is unsubstituted or substituted by halogen such as chlorine, $C_{1-6}$-alkyl such as ethyl, methyl, isopropyl or tert-butyl, or $C_{1-6}$-alkoxy such as methoxy or ethoxy. The preferred meaning of aryl is unsubstituted phenyl. If a dialkyl or monoalkyl-monoaryl succinate is employed, then alkyl may be unbranched or branched, preferably branched, and may contain preferably 1 to 18, in particular 1 to 12, more particularly 1 to 8 and more preferably 1 to 5, carbon atoms. Branched alkyl is preferably sec- or tert-alkyl, for example, isopropyl, sec-butyl, tert-butyl, tert-amyl and cyclohexyl.

Examples of disuccinates are dimethyl succinate, diethyl succinate, dipropyl succinate, dibutyl succinate, dipentyl succinate, dihexyl succinate, diheptyl succinate, dioctyl succinate, diisopropyl succinate, di-sec-butyl succinate, di-tert-butyl succinate, di-tert-amyl succinate, di-[1,1-dimethylbutyl] succinate, di-[1,1,3,3-tetramethylbutyl] succinate, di-[1,1-dimethylpentyl] succinate, di-[1-methyl-ethylbutyl] succinate, di-[1,1-diethylpropyl] succinate, diphenyl succinate, di-[4-methylphenyl] succinate, di-[4-chlorophenyl] succinate, monoethyl-monophenyl succinate, and dicyclohexyl succinate. Most preferably, the starting disuccinate is diisopropyl succinate.

Typically, the nitrile and the disuccinate are used in stoichiometric proportions. It can be advantageous to use the nitrile to be reacted with the disuccinate in more than only stoichiometric proportions. The reaction of the disuccinate with the nitrile is carried out in an organic solvent. Examples of suitable solvents are primary, secondary or tertiary alcohols containing 1 to 10 carbon atoms, for example, methanol, ethanol, n-propanol, isopropanol, n-butanol, sec-butanol, tert-butanol, n-pentanol, 2-methyl-2-butanol, 2-methyl-2-pentanol, 3-methyl-3-pentanol, 2-methyl-2-hexanol, 3-ethyl-3-pentanol, 2,4,4-trimethyl-2-pentanol, or glycols such as ethylene glycol or diethylene glycol; and also ethers such as tetrahydrofuran or dioxan, or glycol ethers such as ethylene glycol methyl ether, ethylene glycol ethyl ether, diethylene glycol monomethyl ether or diethylene glycol monoethyl ether; as well as dipolar aprotic solvents such as acetonitrile, benzonitrile, dimethylformamide, N,N-dimethylacetamide, nitrobenzene, N-methylpyrrolidone; aliphatic or aromatic hydrocarbons such as benzene or benzene substituted by alkyl, alkoxy or halogen, for example, toluene, xylene, anisole or chlorobenzene; or aromatic heterocyclic compounds such as pyridine, picoline or quinoline. In addition, it is also possible to use the nitrile of formula (XI) or (XII) simultaneously as solvent if it is liquid in the temperature range in which the reaction takes place. Mixtures of the above solvents may also be used. It is convenient to use 5 to 20 parts be weight of solvent per 1 part by weight of reactants.

The process according to the invention is carried out in the presence of a strong base.

Suitable strong bases are in particular the alkali metals themselves such as lithium, sodium or potassium, or alkali metal amides such as lithium amide, sodium amide or potassium amide, or alkali metal hydrides such as lithium, sodium or potassium hydride, or alkaline earth metal alcoholates or alkali metal alcoholates which are derived preferably from primary, secondary or tertiary aliphatic alcohols containing from 1 to 10 carbon atoms.

The preferred strong base is an alkali metal alcoholate, the alkali metals being preferably sodium or potassium and the alcoholate being preferably derived from a secondary or tertiary alcohol, for example, sodium or potassium isopropylate, sodium or potassium sec-butylate, sodium or potassium tert-butylate and sodium or potassium tert-amylate.

The strong base is employed in an amount of preferably from about 0.1 to about 10 moles, most preferably from about 1.9 to about 4.0 moles, based on one mole of the disuccinate. Regulation in particle size of the 1,4-diketopyrrolo[3,4-c]pyrroles of formula X relative to the particle size of the unregulated form thereof becomes noticeable with the inclusion of as little as 0.1% of the particle growth regulator relative to the weight of the DPP compound of the formula II. The level of the regulator can be as high as 10% by weight. The preferred range of particle growth regulator is from 0.5 to 4% by weight, the most preferred range is from 0.5% to 2% by weight.

A preferred embodiment is to charge the reaction vessel with the nitrile and the base and then adding the disuccinate in the range of the reaction temperature, which addition order has a particularly advantageous effect on the yield. It is also possible to add the disuccinate and the nitrile simultaneously to the base.

In particular, when using disuccinates containing alkyl radicals and alcoholates which are derived from lower alcohols such as methanol, ethanol, n-propanol, isopropanol or tert-butanol, it may be necessary to remove the lower alcohol formed during the reaction from the reaction medium continuously in order to obtain higher yields.

If an alcohol is used as solvent and an alcoholate as base, it may prove advantageous to choose an alcohol and alcoholate having the same alkyl moieties. It may likewise be advantageous if, in addition, the disuccinate also contains such alkyl groups.

The conditioning step a) is carried out in water containing 0.0-100.0%, preferably 20.0-50.0% of a water-miscible solvent, at a conditioning temperature of 1° C. to the reflux temperature, preferably close to reflux temperature, optionally in the presence of an inorganic acid.

In general water-miscible solvents are selected from water-miscible alcohols, polyols, nitriles, organic acids, amides, esters, ethers, ketones, amines or a mixture of these solvents.

Especially suitable water-miscible solvents include alcohols, in particular $C_{1-4}$-alkyl alcohols, such as methanol, ethanol, n- and isopranol, polyols, like glycols, such as ethylene glycol, diethylene glycol, ethers, like glycol ethers, such as ethylene glycol methyl ether, ethylene glycol ethyl ether, diethylene glycol monomethyl ether or diethylene glycol monoethylether, tetrahydrofuran (THF) and dioxane, organic acids, like acetic acid, ketones, like acetone, amines, such as mono-, di- or trialkylamines, such as propylamine, isopropylamine, diethylamine, dipropylamine, diisopropylamine, triethylamine, tripropylamine, triisopropylamine, bis(1-methyl)propylamine, 1,1-dimethylethylamine and 2-ethylhexylamine, aromatic amines, such as aniline, toluidine or phenylene diamine, and mixtures thereof.

Suitable inorganic acids are hydrochloric, sulphuric and phosphoric acid.

The conditioning step b) is carried out in an aprotic, water-miscible solvent in the presence of 0.0-99.0% water or in nonmiscible solvents with high boiling point or mixtures thereof at a conditioning temperature from 1° C. to the boiling point, most preferably 10-20° C. below the boiling point of the solvent.

Suitable aprotic, water-miscible solvents include acetonitrile, N-methyl-2-pyrrolidone (NMP), gamma-butyrolactone, dimethylsulfoxide (DMSO), N,N-dimethylacetamide (DMA), N,N-dimethylformamide (DMF), and mixtures thereof. Nonmiscible solvents include diphenylether, such as Dowtherm® E, nonmiscible alcohols, such as pentanol, hexanol and heptanol, nonmiscible aromatic solvents like toluene, xylene, o-dichlorobenzene, nonmiscible ketones, nonmiscible ethers and cyclic ethers, nonmiscible amines and aromatic amines, nonmiscible amides and esters and mixtures thereof.

The particle growth regulator of formula II can be added in the heating step (a), the conditioning step (b) or the conditioning step (c).

The process is illustrated below in further detail on the basis of preferred embodiments:

Process A-1:

The synthesis of the DPPs of the formula X is done in the presence of 0.1-20.0%, preferably 0.25-2.0% DPP analogue of the formula II, wherein the DPP analogue is preferably added at the beginning or at the end of the DPP synthesis, just before the conditioning.

The conditioning is carried out in water containing 0.0-100.0%, preferably 20.0-50.0% of a water-miscible solvent, at a conditioning temperature of 1° C. to the reflux temperature, preferably close to reflux temperature.

Process A-2:

The synthesis of the DPPs of the formula X is done in the presence of 0.1-20.0%, preferably 0.25-2.0% of the DPP analogue of formula II, wherein the DPP analogue of formula II is added at the beginning or at the end of the DPP synthesis, just before the first conditioning.

The first conditioning is carried out in water containing 0.0-100.0%, preferably 20.0-50.0% of a water-miscible solvent at a conditioning temperature of 1° C. to the reflux temperature, preferably 0°-40° C., optionally in the presence of 1.0-99.0%, preferably 5.0-20.0% inorganic acid.

The second conditioning is carried out in an aprotic, water-miscible solvent in the presence of 0.0-99.0% water at a conditioning temperature from 1° C. to the boiling point, most preferably 10-20° C. below the boiling point of the solvent or in a non-miscible solvent with a high boiling point at a conditioning temperature from room temperature to the boiling point, preferably 10-20° C. below the boiling point of the solvent.

Process A-3:

The synthesis of the DPPs of formula X is done without the addition of a crystal growth regulator of formula II.

The first conditioning is carried out in water containing 0.0-100.0%, preferably 20.0-50.0% of a water-miscible solvent at a conditioning temperature of 1° C. to the reflux temperature, preferably 1°-40° C., optionally in the presence of 1.0-99.0%, preferably 5.0-20.0% inorganic acid.

The second conditioning is carried out in an aprotic, water-miscible solvent in the presence of 0.0-99.0% water at a conditioning temperature from 1° C. to the boiling point, most preferably 10-20° C. below the boiling point of the solvent or in a non-miscible solvent with a high boiling point at a conditioning temperature from room temperature to the boiling point, preferably 10-20° C. below the boiling point of the solvent in the presence of 0.1-20.0%, preferably 0.25-2.0% of the DPP analogue of formula II.

Diketopyrrolopyrrole analogues, wherein $A^1$ and $A^2$ are radicals of the formula

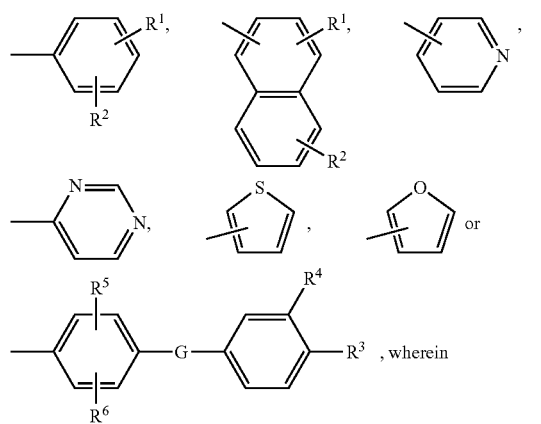

, wherein $R^1$ and $R^2$ are independently of each other hydrogen, halogen, $C_1$-$C_{18}$alkyl, $C_1$-$C_{18}$alkoxy, $C_1$-$C_{18}$alkylmercapto, $C_1$-$C_{18}$alkylamino, $C_1$-$C_{18}$alkoxyrarbonyl, $C_1$-$C_{18}$alkylaminocarbonyl, —CN, —$NO_2$, trifluoromethyl, $C_5$-$C_8$cycloalkyl, —C≡N—($C_1$-$C_{18}$alkyl), phenyl,

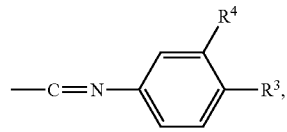

imidazolyl, pyrazolyl, triazolyl, piperazinyl, pyrrolyl, oxazolyl, benzoxazolyl, benzothiazolyl, benzimidazolyl, morpholinyl, piperidinyl or pyrrolidinyl, —$CONX^5X^6$, —$C(O)OX^7$ or —$SO_2X^9$; wherein $X^5$ and $X^6$ are hydrogen, linear or branched $C_{1-10}$-alkyl, $C_{5-10}$-cycloalkyl or $C_{6-10}$-aryl, $X^7$ is hydrogen, linear or branched $C_{1-10}$-alkyl, $C_{5-10}$-cycloalkyl or $C_{6-10}$-aryl, $X^9$ is hydrogen, linear or branched $C_{1-10}$-alkyl, $C_{5-10}$-cycloalkyl, $C_{7-10}$-aralkyl, $C_{6-10}$-aryl or —$NX^{10}X^{11}$, wherein $X^{10}$ and $X^{11}$ are hydrogen, linear or branched $C_{1-10}$-alkyl, $C_{7-10}$-aralkyl or $C_{6-10}$-aryl, G is —$CH_2$—, —$CH(CH_3)$—, —$C(CH_3)_2$—, —CH═N—, —N═N—, —O—, —S—, —SO—, —$SO_2$—, —CONH— or —$NR_7$—, $R^3$ and $R^4$ are independently of each other hydrogen, halogen, $C_1$-$C_6$alkyl, $C_1$-$C_{18}$alkoxy or —CN, $R^5$ and $R^5$ are independently of each other hydrogen, halogen or $C_1$-$C_6$alkyl, and $R^7$ is hydrogen or $C_1$-$C_6$alkyl are preferred, wherein radicals of the formula

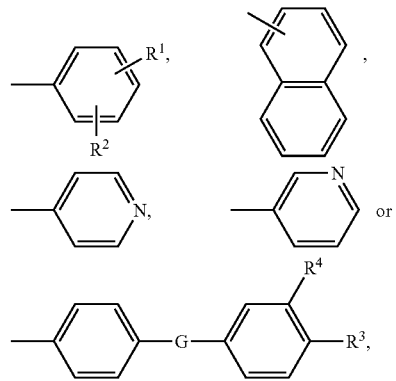

wherein $R^1$ and $R^2$ are independently of each other hydrogen, chloro, bromo, $C_1$-$C_4$alkyl, $C_1$-$C_6$alkoxy, $C_1$-$C_6$alkylamino, phenyl or CN, —$CONX^5X^6$, or —$SO_2X^9$; wherein $X^5$ and $X^6$ are hydrogen, linear or branched $C_{1-4}$-alkyl, $X^9$ is hydrogen, linear or branched $C_{1-4}$-calkyl, $C_{7-10}$-aralkyl, $C_{6-10}$-aryl or —$NX^{10}X^{11}$, wherein $X^{10}$ and $X^{11}$ are hydrogen, linear or branched $C_{1-10}$-alkyl, $C_{7-10}$-aralkyl or $C_{6-10}$-aryl;

G is —O—, —$NR^7$—, —N═N— or —$SO_2$—, $R^3$ and $R^4$ are hydrogen, and $R^7$ is hydrogen, methyl or ethyl are further preferred and diketopyrrolopyrrole analogues, wherein $A^1$ and $A^2$ are radicals of the formula

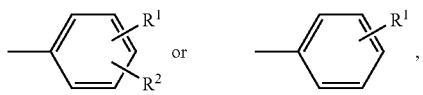

wherein $R^1$ and $R^2$ are independently of each other hydrogen, $C_{1-4}$-alkyl, such as methyl or tert-butyl, halogen, such as chloro or bromo, $C_{1-4}$-alkoxy or $C_{1-4}$-thioalkyl, phenyl or CN or —$SO_2X^9$, wherein $X^9$ is $C_{1-4}$-alkyl, phenyl, benzyl or $NX^{10}X^{11}$, wherein $X^{10}$ and $X^{11}$ are hydrogen, $C_{1-4}$-alkyl, benzyl or phenyl are particularly preferred.

$A^3$ is preferably hydrogen, $C_1$-$C_8$alkyl such as methyl, ethyl, n-propyl, isopropyl, n-butyl, sec.-butyl, isobutyl, tert.-butyl, n-pentyl, 2-pentyl, 3-pentyl, 2,2-dimethylpropyl, n-hexyl, n-heptyl, n-octyl, 1,1,3,3-tetramethylbutyl and 2-ethylhexyl, Y—$R^{32}$ wherein Y is —C(O)— and $R^{32}$ is

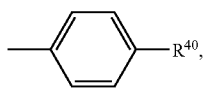

wherein $R^{40}$ is $C_1$-$C_4$alkyl, —O—$C_1$-$C_4$alkyl, or —S—$C_1$-$C_4$alkyl and —$(CH_2)_m$—Ar wherein m is 1 and Ar is a group of the formula

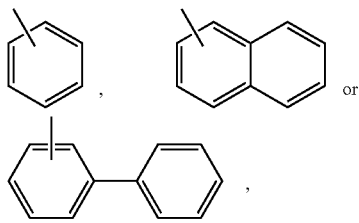

which can be substituted one to three times with $C_1$-$C_8$alkyl, $C_1$-$C_8$alkoxy, halogen or phenyl.

$C_1$-$C_{18}$alkyl is typically linear or branched—where possible—and examples of $C_1$-$C_{18}$alkyl are methyl, ethyl, n-propyl, isopropyl, n-butyl, sec.-butyl, isobutyl, tert.-butyl, n-pentyl, 2-pentyl, 3-pentyl, 2,2-dimethylpropyl, n-hexyl, n-heptyl, n-octyl, 1,1,3,3-tetramethylbutyl and 2-ethylhexyl, n-nonyl, decyl, undecyl, dodecyl, tetradecyl, pentadecyl, hexadecyl, heptadecyl and octadecyl. $C_1$-$C_8$alkyl such as methyl, ethyl, n-propyl, isopropyl, n-butyl, sec.-butyl, isobutyl, tert.-butyl, n-pentyl, 2-pentyl, 3-pentyl, 2,2-dimethylpropyl, n-hexyl, n-heptyl, n-octyl, 1,1,3,3-tetramethylbutyl and 2-ethylhexyl is preferred. $C_1$-$C_4$alkyl such as methyl, ethyl, n-propyl, isopropyl, n-butyl, sec.-butyl, isobutyl or tert.-butyl is particularly preferred. The term "$C_2$-$C_{18}$alkenyl group" means an unsaturated linear or branched aliphatic hydrocarbon group containing one or more double bonds, in particular $C_{2-8}$-alkenyl, such as vinyl, allyl, 2-propen-2-yl, 2-buten-1-yl, 3-buten-1-yl, 1,3-butadien-2-yl, 2-penten-1-yl, 3-penten-2-yl, 2-methyl-1-buten-3-yl, 2-methyl-3-buten-2-yl, 3-methyl-2-buten-1-yl and 1,4-pentadien-3-yl. The term "$C_2$-$C_{18}$alkynyl group" means an unsaturated aliphatic hydrocarbon group containing a triple bond, in particular $C_2$-$C_8$-alkynyl such as ethynyl, 1-propyn-1-yl, 2-butyn-1-yl, 3-butyn-1-yl, 2-pentyn-1-yl and 3-pentyn-2-yl.

Examples of $C_1$-$C_{18}$alkoxy, which can be linear or branched, are methoxy, ethoxy, n-propoxy, isopropoxy, n-butoxy, sec.-butoxy, isobutoxy, tert.-butoxy, n-pentoxy, 2-pentoxy, 3-pentoxy, 2,2-dimethylpropoxy, n-hexoxy, n-heptoxy, n-octoxy, 1,1,3,3-tetramethylbutoxy and 2-ethylhexoxy, wherein $C_1$-$C_4$alkoxy such as methoxy, ethoxy, n-propoxy, isopropoxy, n-butoxy, sec.-butoxy, isobutoxy and tert.-butoxy is preferred. Examples of $C_1$-$C_{18}$alkylmercapto are the same groups as mentioned for the alkoxy groups, except that the oxygen atom of the ether linkage is replaced by a sulphur atom. Examples and preferences for $C_1$-$C_{18}$alkyl in $C_1$-$C_{18}$alkylamino and $C_1$-$C_{18}$alkylaminocarbonyl are the same as mentioned for $C_1$-$C_{18}$alkyl. Examples and preferences for $C_1$-$C_{18}$alkoxy in $C_1$-$C_{18}$alkoxycarbonyl are the same as mentioned for $C_1$-$C_{18}$alkoxy.

The term "aryl group" is typically $C_6$-$C_{24}$aryl, such as phenyl, 1-naphthyl, 2-naphthyl, 4-biphenyl, phenanthryl, terphenyl, pyrenyl, 2- or 9-fluorenyl or anthracenyl, preferably $C_6$-$C_{12}$aryl such as phenyl, 1-naphthyl, 2-naphthyl, 4-biphenyl, which may be unsubstituted or substituted.

The term "aralkyl group" is typically $C_7$-$C_{24}$aralkyl, such as benzyl, 2-benzyl-2-propyl, β-phenylethyl, α,α-dimethylbenzyl, ω-phenylbutyl, ω,ω-dimethyl-ω-phenylbutyl, ω-phenyldodecyl, ω-phenyloctadecyl, ωphenyleicosyl or ω-phenyldocosyl, preferably $C_7$-$C_{18}$aralkyl such as benzyl, 2-benzyl-2-propyl, β-phenylethyl, α,α-dimethylbenzyl, ω-phenylbutyl, ω,ω-dimethyl-ω-phenylbutyl, ω-phenyldodecyl or ω-phenyloctadecyl, and particularly preferred $C_7$-$C_{12}$aralkyl such as benzyl, 2-benzyl-2-propyl, β-phenylethyl, α,α-dimethylbenzyl, ω-phenyl-butyl, or ω,ω-dimethyl-ω-phenyl-butyl, in which both the aliphatic hydrocarbon group and aromatic hydrocarbon group may be unsubstituted or substituted.

Examples of $C_5$-$C_8$cycloalkyl are cyclopentyl, cyclohexyl, cycloheptyl and cyclooctyl, which may be unsubstituted or substituted. The term "$C_5$-$C_8$cycloalkenyl group" means an unsaturated alicyclic hydrocarbon group containing one or more double bonds, such as cyclopentenyl, cyclopentadienyl and cyclohexenyl, which may be unsubstituted or substituted.

The term "heteroaryl" is a ring with five to seven ring atoms, wherein nitrogen, oxygen or sulfur are the possible hetero atoms, and is typically an unsaturated heterocyclic radical with five to 18 atoms having at least six conjugated π-electrons such as thienyl, benzo[b]thienyl, dibenzo[b,d] thienyl, thianthrenyl, furyl, furfuryl, 2H-pyranyl, benzofuranyl, isobenzofuranyl, dibenzofuranyl, phenoxythienyl, pyrrolyl, imidazolyl, pyrazolyl, pyridyl, bipyridyl, triazinyl, pyrimidinyl, pyrazinyl, pyridazinyl, indolizinyl, isoindolyl, indolyl, indazolyl, purinyl, quinolizinyl, quinolyl, isoquinolyl, phthalazinyl, naphthyridinyl, quinoxalinyl, quinazolinyl, cinnolinyl, pteridinyl, carbazolyl, carbolinyl, benzotriazolyl, benzoxazolyl, phenanthridinyl, acridinyl, perimidinyl, phenanthrolinyl, phenazinyl, isothiazolyl, phenothiazinyl, isoxazolyl, furazanyl or phenoxazinyl.

Examples of a halogen atom are fluorine, chlorine, bromine and iodine.

If the above-mentioned substituents can be substituted, possible substituents are $C_1$-$C_8$alkyl, a hydroxyl group, a mercapto group, $C_1$-$C_8$alkoxy, $C_1$-$C_8$alkylthio, halogen, halo-$C_1$-$C_8$alkyl, a cyano group, an aldehyde group, a ketone group, a carboxyl group, an ester group, a carbamoyl group, an amino group, a nitro group, a silyl group or a siloxanyl group, The present invention relates also to the use of the inventive DPP analogues of the general formula I for the preparation of inks for printing inks in printing processes, for flexographic printing, screen printing, packaging printing, security ink printing, intaglio printing or offset printing, for pre-press stages and for textile printing, for office, home applications or graphics applications, such as for paper goods, for example, for ballpoint pens, felt tips, fiber tips, card, wood, (wood) stains, metal, inking pads or inks for impact printing processes (with impact-pressure ink ribbons), for the preparation of colorants for coating materials, for industrial or commercial use, for textile decoration and industrial marking, for roller coatings or powder coatings or for automotive finishes, for high-solids (low-solvent), water-containing or metallic coating materials or for pigmented formulations for aqueous paints, for the preparation of pigmented plastics for coatings, fibers, platters or mold carriers, for the preparation of non-impact-printing material for digital printing, for the thermal wax transfer printing process, the ink jet printing process or for the thermal transfer printing process, and also for the preparation of color filters, especially for visible light in the range from 400 to 700 nm, for liquid-crystal displays (LCDs) or charge combined devices (CCDs) or for the preparation of cosmetics or for the preparation of polymeric Ink particles, toners, dye lasers, dry copy toners liquid copy toners, or electrophotographic toners, and electroluminescent devices.

Illustrative examples of suitable organic materials of high molecular weight which can be colored with the inventive fluorescent DPP analogues of the general formula I are vinyl polymers, for example polystyrene, poly-α-methylstyrene, poly-p-methylstyrene, poly-p-hydroxystyrene, poly-p-hydroxyphenylstyrene, polymethyl methacrylate and polyacrylamide as well as the corresponding methacrylic compounds, poly(methyl) maleate, polyacrylonitrile, polymethacrylonitrile, polyvinyl chloride, polyvinyl fluoride, polyvinylidene chloride, polyvinylidene fluoride, polyvinyl acetate, polymethyl vinyl ether and polybutyl vinyl ether; polymers which are derived from maleinimide and/or maleic anhydride, such as copolymers of maleic anhydride with styrene; poly(vinyl)pyrrolidone; ABS; ASA; polyamides; polyimides; polyamidimides; polysulfones; polyether sulfones; polyphenylene oxides; polyurethanes; polyureas; polycarbonates; polyarylenes; polyarylene sulfides; polyepoxides; polyolefins such as polyethylene and polypropylene; polyalkadienes; biopolymers and the derivatives thereof e.g. cellulose, cellulose ethers and esters such as ethylcellulose, nitrocellulose, cellulose acetate and cellulose butyrate, starch, chitin, chitosan, gelatin, zein; natural resins; synthetic resins such as alkyd resins, acrylic resins, phenolic resins, epoxide resins, aminoformaldehyde resins such as urea/formaldehyde resins and melamine/formaldehyde resin; vulcanized rubber; casein; silicone and silicone resins; rubber, chlorinated rubber; and also polymers which are used, for example, as binders in paint systems, such as novolaks which are derived from $C_1$-$C_6$-aldehydes such as formaldehyde and acetaldehyde and a binuclear or mononuclear, preferably mononuclear, phenol which, if desired, is substituted by one or two $C_1$-$C_9$alkyl groups, one or two halogen atoms or one phenyl ring, such as o-, m- or p-cresol, xylene, p-tert.-butylphenol, o-, m- or p-nonylphenol, p-chlorophenol or p-phenylphenol, or a compound having more than one phenolic group such as resorcinol, bis(4-hydroxyphenyl)methane or 2,2-bis(4-hydroxyphenyl)propane; as well as suitable mixtures of said materials.

Particularly preferred high molecular weight organic materials, in particular for the preparation of a paint system, a printing ink or ink, are, for example, cellulose ethers and esters, e.g. ethylcellulose, nitrocellulose, cellulose acetate and cellulose butyrate, natural resins or synthetic resins (polymerization or condensation resins) such as aminoplasts, in particular urea/formaldehyde and melamine/formaldehyde resins, alkyd resins, phenolic plastics, polycarbonates, polyolefins, polystyrene, polyvinyl chloride, polyamides, polyurethanes, polyester, ABS, ASA, polyphenylene oxides, vulcanized rubber, casein, silicone and silicone resins as well as their possible mixtures with one another.

It is also possible to use high molecular weight organic materials in dissolved form as film formers, for example boiled linseed oil, nitrocellulose, alkyd resins, phenolic resins, melamine/formaldehyde and urea/formaldehyde resins as well as acrylic resins.

Said high molecular weight organic materials may be obtained singly or in admixture, for example in the form of granules, plastic materials, melts or in the form of solutions, in particular for the preparation of spinning solutions, paint systems, coating materials, inks or printing inks.

In a particularly preferred embodiment of this invention, the inventive DPPs of the general formula I are used for the mass coloration of polyvinyl chloride, polyamides and, especially, polyolefins such as polyethylene and polypropylene as well as for the preparation of paint systems, including powder coatings, inks, printing inks, color filters and coating colors. Illustrative examples of preferred binders for paint systems are alkyd/melamine resin paints, acryvmelamine resin paints, cellulose acetate/cellulose butyrate paints and two-pack system lacquers based on acrylic resins which are crosslinkable with polyisocyanate.

According to observations made to date, the inventive DPPs of the general formula I can be added in any desired amount to the material to be colored, depending on the end use requirements. In the case of high molecular weight organic materials, for example, the fluorescent DPP analogues of the general formula I prepared according to this invention can be used in an amount in the range from 0.01 to 50, preferably from 0.01 to 5% by weight, based on the total weight of the colored high molecular weight organic material.

Hence, another embodiment of the present invention relates to a composition comprising (a) 0.01 to 50, preferably 0.01 to 5, particularly preferred 0.01 to 2% by weight, based on the total weight of the colored high molecular organic material, of a DPP of the general formula I according to the present invention, and (b) 99.99 to 50, preferably 99.99 to 95, particularly preferred 99.99 to 98% by weight, based on the total weight of the colored high molecular organic material, of a high molecular organic material, and (c) if desired, customary additives such as rheology improvers, dispersants, fillers, paint auxiliaries, siccatives, plasticizers, UV-stabilizers, and/or additional pigments or corresponding precursors in effective amounts, such as e.g. from 0 to 50% by weight, based on the total weight of (a) and (b).

To obtain different shades, the inventive DPPs of the general formula I may advantageously be used in admixture with fillers, transparent and opaque white, colored and/or black pigments as well as customary luster pigments in the desired amount.

For the preparation of paint systems, coating materials, color filters, inks and printing inks, the corresponding high molecular weight organic materials, such as binders, synthetic resin dispersions etc. and the inventive DPPs of the general formula I are usually dispersed or dissolved together, if desired together with customary additives such as dispersants, fillers, paint auxiliaries, siccatives, plasticizers and/or additional pigments or pigment precursors, in a common solvent or mixture of solvents. This can be achieved by dispersing or dissolving the individual components by themselves, or also several components together, and only then bringing all components together, or by adding everything together at once. Hence, a further embodiment of the present invention relates to a method of using the inventive DPPs of the general formula I for the preparation of dispersions and the corresponding dispersions, and paint systems, coating materials, color filters, inks and printing inks comprising the inventive DPPs of the general formula I.

A particularly preferred embodiment relates to the use of the inventive fluorescent DPPs of the general formula I for the preparation of fluorescent tracers for e.g. leak detection of fluids such as lubricants, cooling systems etc., as well as to fluorescent tracers or lubricants comprising the inventive DPPs of the general formula I. Usually, such lubricant compositions, e.g. for a refrigerant, comprise an oil selected from the group consisting of naphthalenic oils, paraffinic oils, alkylated benzene oils, polyalkyl silicate oils, polyglycols, esters, polyether polyols, polyvinyl ethers, polycarbonates, fluorinated silicones, perfluoroethers, aromatic compounds with fluoroalkyloxy or fluoroalkylthio substituents. The amount of the inventive DPP of the general formula I in the lubricant is chosen generally in an amount of from 100 to 1000 ppm. If the inventive compound I is water-soluble, it could be used as tracer in water as well.

A particular embodiment of this invention concerns ink jet inks comprising the inventive DPPs of the general formula I.

For the coloring of high molecular weight organic material, the inventive DPPs of the general formula I, optionally in the form of masterbatches, usually are mixed with the high molecular weight organic materials using roll mills, mixing apparatus or grinding apparatus. Generally, the pigmented material is subsequently brought into the desired final form by conventional processes, such as calandering, compression molding, extrusion, spreading, casting or injection molding. In order to prepare non-rigid moldings or to reduce their brittleness it is often desired to incorporate so-called plasticizers into the high molecular weight organic materials prior to forming. Examples of compounds which can be used as such plasticizers are esters of phosphoric acid, phthalic acid or sebacic acid. The plasticizers can be added before or after the incorporation of the inventive DPP analogues of the general formula I into the polymers. It is also possible, in order to achieve different hues, to add fillers or other coloring constituents such as white, color or black pigments in desired amounts to the high molecular weight organic materials in addition to the inventive DPP analogues of the general formula I.

For colouring lacquers, coating materials and printing inks the high molecular weight organic materials and the inventive DPPs of the general formula I, alone or together with additives, such as fillers, other pigments, siccatives or plasticizers, are generally dissolved or dispersed in a common organic solvent or solvent mixture. In this case it is possible to adopt a procedure whereby the individual components are dispersed or dissolved individually or else two or more are dispersed or dissolved together and only then are all of the components combined.

The present invention additionally relates to inks comprising a coloristically effective amount of the inventive DPP of the general formula I.

Processes for producing inks especially for ink jet printing are generally known and are described for example in U.S. Pat. No. 5,106,412.

When mixing a DPP of the general formula I with polymeric dispersants it is preferred to use a water-dilutable organic solvent.

The weight ratio of the pigment dispersion to the ink in general is chosen in the range of from 0.001 to 75% by weight, preferably from 0.01 to 50% by weight, based on the overall weight of the ink.

The preparation and use of color filters or color-pigmented high molecular weight organic materials are well-known in the art and described e.g. in Displays 14/2, 1151 (1993), EP-A-784085, or GB-A-2,310,072.

The color filters can be coated for example using inks, especially printing inks, which can comprise the inventive DPPs of the general formula I or can be prepared for example by mixing a DPP of the general formula I with chemically, thermally or photolytically structurable high molecular weight organic material (so-called resist). The subsequent preparation can be carried out, for example, in analogy to EP-A-654 711 by application to a substrate, such as a LCD, subsequent photostructuring and development.

The present invention relates, moreover, to toners comprising a DPP of the general formula I or a high molecular weight organic material coloured with a DPP of the general formula I in a coloristically effective amount.

In a particular embodiment of the process of the invention, toners, coating materials, inks or colored plastics are prepared by processing masterbatches of toners, coating materials, inks or colored plastics in roll mills, mixing apparatus or grinding apparatus.

The present invention additionally relates to colorants, colored plastics, polymeric ink particles, or non-Impact-printing material comprising an inventive DPP of the general formula I or a high molecular weight organic material coloured with a DPP of the general formula I in a coloristically effective amount.

A coloristically effective amount of the pigment dispersion according to this invention comprising an inventive DPP I denotes in general from 0.0001 to 99.99% by weight, preferably from 0.001 to 50% by weight and, with particular preference, from 0.01 to 5% by weight, based on the overall weight of the material pigmented therewith.

Further, the inventive compounds I can be used for textile application and for the dying of paper.

The following examples illustrate various embodiments of the invention, but the scope of the invention is not limited thereto.

EXAMPLES

Example 1

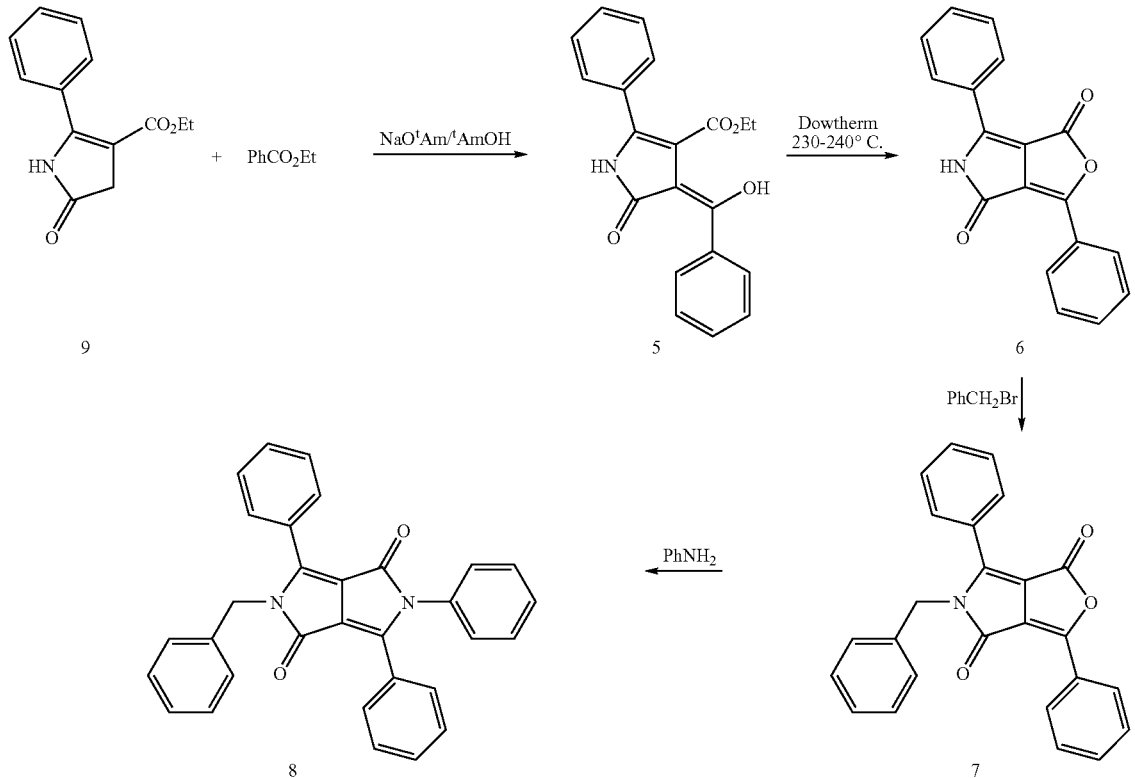

Compound 5:

To pre-dried t-amyl alcohol (40 ml) was added sodium (1.50 g, 0.0652 mol) with stirring under nitrogen and the mixture heated to reflux (105-110° C.) until all the sodium dissolved. The solution was cooled to 25° C., then the lactam ester 9 (5.03 g, 0.0218 mol) and ethyl benzoate (3.27 g, 0.0218 mol) were added. The mixture was then heated to reflux for 5.5 h during which time an orange solution developed. The cooled mixture was added to an ice-cooled mixture of methanol (10 ml) and water (50 ml), acidified dropwise with concentrated hydrochloric acid (3 ml) then extracted with tetrahydrofuran/diethyl ether, dried ($Na_2SO_4$) and concentrated. Recrystallisation from aqueous ethanol yielded amber coloured crystals.

Yield 2.38 g (33%), m.p. 156-157° C. (Found: C, 71.5; H, 5.2; N, 4.2. $C_{20}H_{17}NO_4$ requires C, 71.6; H, 5.1; N, 4.2%). $\delta_H$ 0.67 (3H, t, J 7.2, $OCH_2CH_3$), 3.56 (2H, q, $OCH_2CH_3$), 7.40-7.56 (6H, m, m-lp-Ar—H), 7.62-7.68 (4H, m, o-Ar—H), 9.52 (1H, br. s, NH). m/z 335 ($M^+$, 54%), 289 (100), 105 (56).

Compound 6:

A mixture of compound 5 (10 g, 0.0299 mol) and Dowtherm A (200 ml) was heated to 230-240° C. under nitrogen for 64 h. The solution was then cooled to 25° C. and added dropwise to petrol ether 40-60 (300 ml) upon which a fluorescent orange solid precipitated. This was filtered off, washed with further hexane and dried in vacua. Yield 3.48 g (40%). (Found: C, 74.9; H, 4.2; N, 4.8%. $C_{18}H_{11}NO_3$ requires C, 74.7; H, 3.8; N, 4.8). m/z289 ($M^+$, 100%), 204 (20), 105 (35), 77 (35).

Compound 7:

To a suspension of sodium hydride (0.20 g, 55-65% dispersion in mineral oil) in tetrahydroturan (100 ml) was added compound 6 under nitrogen at 25° C. (1.0 g, 0.0034 mol) and the mixture was heated briefly to reflux during 5 mins. The solution was cooled to 25° C., then benzyl bromide (0.70 g, 0.0041 mol) was added. The solution was heated to reflux during 19 h, then cooled. Water (50 ml) was added and the mixture extracted with a tetrahydrofuran/ethyl acetate solvent mixture. The organic extracts were concentrated and the residue mixed with petrol ether 40-60 and treated in an ultrasonic bath for 20 mins. The product was filtered off and dried in vacua. Yield 0.97 g (74%). (Found: C, 78.8; H, 4.9; N, 3.6%. $C_{25}H_{17}NO_3$ requires C, 79.1; H, 4.5; N, 3.7). m/z379 ($M_+$, 35%), 105 (50), 91 (100), 77 (20).

Compound 8:

A mixture of compound 7 (10 g, 0.0264 mol), N,N'-dicyclohexylcarbodiimide (13.5 g, 0.0655 mol), dichloromethane (300 ml), trifluoroacetic acid (3 drops) and aniline (5 g, 0.0538 mol) was stirred under nitrogen for 16 h at 40° C. Further aniline (15 g, 0.1613 mol) and N,N'-dicyclohexylcarbodiimide (10 g, 0.0485 mol) were added and heating continued for 24 h. The mixture was then concentrated. The residue was recrystallised from 1,4-dioxan then washed with hot isopropyl alcohol, methanol and water then dried in vacuo. Fluorescent orange solid, yield 1.87 g, (16%). (Found: C, 81.2; H, 5.3; N, 6.4%. $C_{31}H_{22}N_2O_2$ requires C, 81.9; H, 4.9; N, 6.2). m/z 454 (M$^+$, 100%).

Example 2

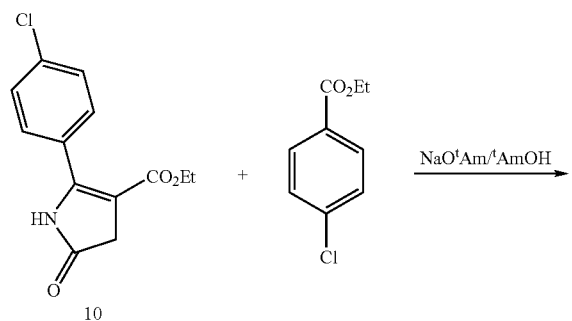

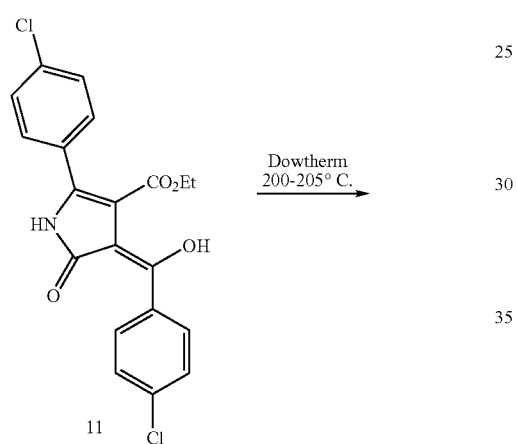

Compound 11:
To pre-dried t-amyl alcohol (230 ml) was added sodium (6.82 g, 0.2967 mol) with stirring under nitrogen and the mixture heated to reflux (105-110° C.) until all the sodium dissolved. The solution was cooled to 70° C. and then the lactam ester 10 (26.29 g, 0.0989 mol) and ethyl 4-chlorobenzoate (18.27 g, 0.0990 mol) were added. The mixture was then heated to reflux for 22 h during which time an orange solution developed. The mixture was then cooled and acidified with 10% hydrochloric acid (250 ml), then extracted with tetrahydrofuran/ethyl acetate, the organic extracts washed with water and then concentrated. The solid residue was recrystallised from an ethanol/isopropylalcohol/water mixed solvent system to a yield beige coloured crystals which were filtered off and dried in vacuo. Yield 31.36 g (78%). Found: C, 59.4; H, 4.1; N, 3.7; Cl, 17.4%. $C_{20}H_{15}Cl_{12}O_4N$ requires C, 59.4; H, 3.7; N,3.5; Cl, 17.5).

Compound 12:
A mixture of compound 11 (15.0 g, 0.0371 mol) and Dowtherm A (300 ml) was heated to 205-210° C. during 48 h then cooled. The mixture was then added dropwise to petrol ether 40-60 (1 l) and the fluorescent purple was filtered off, washed with further petrol and dried in vacuo. Yield 8.95 g (68%). (Found: C, 60.4; H, 2.8; N, 3.9%. $C_{18}H_8Cl_2NO_3$ requires C ,60.5; H, 2.3; N, 3.9). m/z357 (M$^+$, 100%), 139 (100), 111 (85), 75 (35).

Example 3

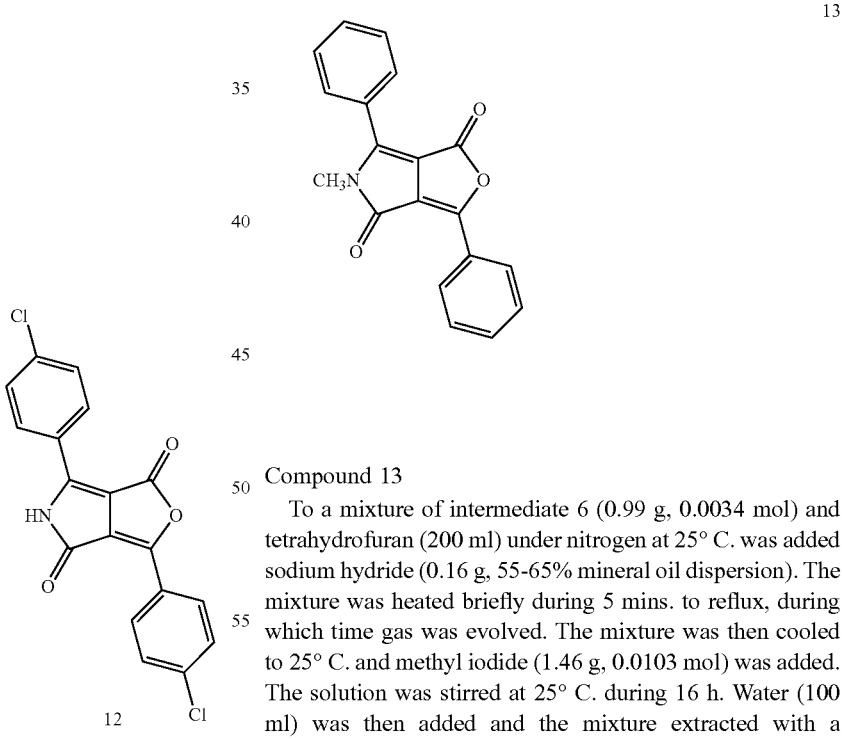

Compound 13
To a mixture of intermediate 6 (0.99 g, 0.0034 mol) and tetrahydrofuran (200 ml) under nitrogen at 25° C. was added sodium hydride (0.16 g, 55-65% mineral oil dispersion). The mixture was heated briefly during 5 mins. to reflux, during which time gas was evolved. The mixture was then cooled to 25° C. and methyl iodide (1.46 g, 0.0103 mol) was added. The solution was stirred at 25° C. during 16 h. Water (100 ml) was then added and the mixture extracted with a tetrahydrofuran/ethyl acetate mixed solvent. The combined organic extracts were then concentrated, redissolved in DMSO (20 ml) and added dropwise to water (200 ml). The fluorescent orange precipitate was filtered off, washed with water and dried in vacuo. Yield 0.96 g (93%). (Found C, 75.2; H, 4.5; N, 4.6%. $C_{19}H_{13}NO_3$ requires C, 75.2; H, 4.3; N, 4.6).

Example 4

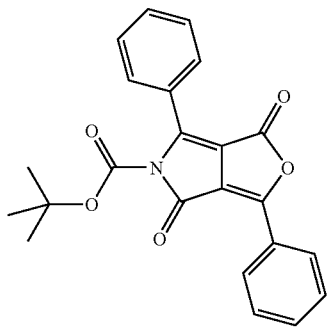

Compound 14

A mixture of intermediate 6 (0.74 g, 0.0026 mol), di-t-butyl dicarbonate (1.34 g, 0.0061 mol), 4-(N,N')-dimethylaminopyridine (0.05 g, 0.0004 mol) and tetrahydrofuran (100 ml) was stirred at 25° C. under nitrogen for 24 h. The reaction mixture was concentrated, then the residue was mixed with methanol (10 ml) and the solid precipitate was filtered off, washed with methanol (5 ml) and dried in vacuo. Fluorescent yellow solid, yield 0.97 g (96%).

Example 5

1.0 g of the DPP analogue 8 was mixed with 63.0 g of polyvinyl chloride, 3.0 g of epoxidized soya oil, 2.0 g of barium/cadmium thermal stabilizer and 32.0 g of dioctyl phthalate, and the mixture was processed on a roller mill at 160° C. for 8 minutes to give a thin sheet. The PVC sheet thus produced is characterized by its very strong fluorescent yellow-orange color.

Example 6

In a 200 ml 4-neck flat bottom reactor equipped with a glass stirrer, a thermometer, a nitrogen inlet tube, a bubble counter and an addition funnel 60.0 g t-amylalcohol techn. and 5.24 g solid sodium were poured. It was heated to 130° C. ext. temperature (int. temp. 110° C.) and a small amount of iron(III) trichloride was added. After the solid sodium has completely disappeared, a mixture of 14.90 g p-chlorobenzonitrile, 14.27 g diisopropylsuccinimide and 42.70 g t-amylalcohol was added within 2 hours. The temperature was decreased to 85° C. (int.) and the reaction mixture was stirred for 2 hrs. The temperature is then decreased to 40° C. and 0.32 g of compound 6 described in example 1 were added. The reaction mixture was then transferred within 15 min. in another reactor, poured into a mixture of 275 ml demineralised water, 275 ml methanol and 120 ml sulphuric acid at 40° C. The pigment was conditioned during 18 hrs. After filtration and drying the obtained dark red pigment powder was poured into 300 ml dimethylacetamide and further conditioned for 5 hrs at 140° C. 13.70 g (71%) of a bright red pigment which in comparison to the pigment of comparative example 1 exhibits a purer, brighter and yellower shade in mass tone, along with a higher opacity. The gloss at 20° C. was slightly better than DPP Red BO. In white reduction, the pigment showed equal colour strength. In white reduction 5:95, the weather stability (2000 h WOM) was comparable to DPP Red BO.

Test Method:

4.0 g untreated pigment were added to 46.0 g AM-paint prepared as described below. The paint at 8% pigment conc. was dispersed 1 hr. in Skandex with 200 g glass beads having a diameter of 2 mm. The dispersed paint is drawn down (100 μm) on a Mylar sheet and poured on a glass plate. After 10 minutes, the Mylar sheet and the glass plate were allowed to dry 30 minutes at 130° C. in a hot air oven. The Mylar sheet had the following colour properties (Datacolor 3890 calorimeter): lightness L*, chroma C*, hue h and opacity (as ΔTr. over black). The contrast paper was a clean and new standard Leneta. From the poured out glass plates the gloss at 20° angle using a gloss meter ZGM 20° from Zehntner Electronics Co. (Switzerland) was determined.

A white reduction containing 5 parts of pigment and 95 parts of white pigment was also prepared: 3.27 g of the previously prepared mass tone paint were added to 26.73 g white AM-paint (description below) and mixed with a simple glass stirrer to yield 30 g white reduction, which is drawn down on a Mylar sheet (100 μm). From the Mylar sheet the colour strength was assessed.

Preparation of the AM-paint

| Mass tone: | 60.00 parts by weight | Bayer Alkydal F 310, 60% in solvent naphtol |
| --- | --- | --- |
| | 16.00 parts by weight | Cytec Cymel 327, 90% in isobutanol |
| | 19.00 parts by weight | xylol |
| | 2.00 parts by weight | butanol |
| | 2.00 parts by weight | 1-methoxy-2-propanol |
| | 1.00 parts by weight | silicone oil A, 1% in xylol |
| White reduction: | 20.00 parts by weight | titanium dioxide Kronos 2310 |
| | 47.67 parts by weight | Bayer Alkydal F 310, 60% in solvent naphtol |
| | 12.75 parts by weight | Cytec Cymel 327, 90% in butanol |
| | 0.50 parts by weight | Aerosil 200 |
| | 1.59 parts by weight | 1-methoxy-2-propanol |
| | 1.59 parts by weight | butanol |
| | 15.10 parts by weight | xylol |
| | 0.80 parts by weight | silicone oil A, 1% in xylol |

Comparative Example 1

Example 6 was repeated except that no compound 6 was added. After filtration and drying in an oven under vacuum 16.03 g (83%) bright red pigment exhibiting colour properties comparable to the 'state-of-the-art' (commercial DPP Red BO) were obtained. The weather stability of this pigment is also comparable to the 'state-of-the-art' (2000 hrs WOM, white reduction 5:95).

The invention claimed is:

1. A process for the preparation of diketopyrrolopyrroles of the formula

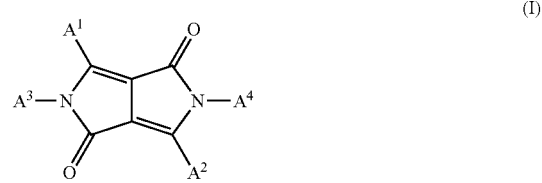

(I)

comprising the steps of:

reacting a compound of the formula

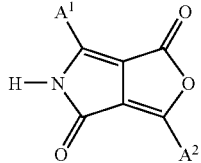
(IV)

with a compound of $A^3$-X (V), wherein $A^1$ and $A^2$ are $C_1$-$C_{18}$alkyl, $C_2$-$C_{18}$alkenyl, $C_2$-$C_{18}$alkynyl, $C_5$-$C_8$cycloalkyl, $C_5$-$C_8$cycloalkenyl, aryl or heteroaryl, $A^3$ is hydrogen, $C_1$-$C_{18}$alkyl, cyanomethyl, $Ar^3$, —$CR^{30}R^{31}$—$(CH_2)_m$—$Ar^3$ or Y—$R^{32}$, wherein $R^{30}$ and $R^{31}$ independently of each other stand for hydrogen or $C_1$-$C_4$alkyl, or phenyl which can be substituted up to three times with $C_1$-$C_3$alkyl, $Ar^3$ stands for aryl, $C_5$-$C_8$cycloalkyl, $C_5$-$C_8$cycloalkenyl or heteroaryl, which can be substituted one to three times with $C_1$-$C_8$alkyl, $C_1$-$C_8$alkoxy, halogen or phenyl, which can be substituted with $C_1$-$C_8$alkyl or $C_1$-$C_8$alkoxy one to three times, and m stands for 0, 1, 2, 3 or 4, Y is —C(O)—, —C(O)O—, —C(O)NH—, —$SO_2$NH— or —$SO_2$— and $R^{32}$ is $C_1$-$C_{18}$alkyl, $Ar^3$, or aralkyl, and $A^4$ is $C_1$-$C_{18}$alkyl or $Ar^3$ where X is a leaving group, to give a compound of the formula

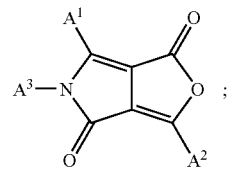
(II)

and ii) reacting the compound of formula (II) with a primary amine of the formula $A^4$—$NH_2$ (III).

2. The process according to claim 1, wherein the compound of the formula IV is obtained by heating a compound of the formula

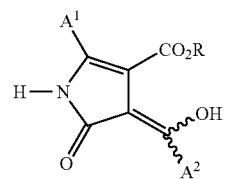
(VI)

in an inert solvent, wherein $A^1$ and $A^2$ have the meanings as given in claim 1 and R is $C_1$-$C_{18}$alkyl, aryl, or aralkyl, which can be substituted one to three times with $C_1$-$C_8$alkyl, $C_1$-$C_8$alkoxy, or halogen.

* * * * *